(12) United States Patent
Balboa et al.

(10) Patent No.: US 10,888,312 B2
(45) Date of Patent: Jan. 12, 2021

(54) SUTURE SECURING ASSEMBLIES

(71) Applicant: Smith & Nephew, Inc., Memphis, TN (US)

(72) Inventors: Marc Joseph Balboa, Hopkinton, MA (US); Geoffrey Ian Karasic, Milton, MA (US); Matthew Edwin Koski, Westford, MA (US); Nehal Navinbhai Patel, Boston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 89 days.

(21) Appl. No.: 16/320,616

(22) PCT Filed: Jul. 26, 2017

(86) PCT No.: PCT/US2017/044004
§ 371 (c)(1),
(2) Date: Jan. 25, 2019

(87) PCT Pub. No.: WO2018/022787
PCT Pub. Date: Feb. 1, 2018

(65) Prior Publication Data
US 2019/0167254 A1   Jun. 6, 2019

Related U.S. Application Data

(60) Provisional application No. 62/447,551, filed on Jan. 18, 2017, provisional application No. 62/430,461,
(Continued)

(51) Int. Cl.
*A61B 17/04* (2006.01)
*A61F 2/08* (2006.01)
*A61B 17/00* (2006.01)

(52) U.S. Cl.
CPC ........ *A61B 17/0401* (2013.01); *A61F 2/0811* (2013.01); *A61B 2017/00004* (2013.01);
(Continued)

(58) Field of Classification Search
CPC ...... A61B 17/0401; A61B 2017/00004; A61B 2017/0409; A61B 2017/0412;
(Continued)

(56) References Cited

U.S. PATENT DOCUMENTS

2009/0287227 A1* 11/2009 Newell .............. A61B 17/0401
606/148
2014/0257385 A1* 9/2014 Lunn ................. A61B 17/0401
606/232
(Continued)

*Primary Examiner* — Suba Ganesan
*Assistant Examiner* — Aren Patel
(74) *Attorney, Agent, or Firm* — Burns & Levinson, LLP; Joseph M. Maraia; Mario Schepper Grolnic

(57) ABSTRACT

A suture securing assembly comprises a two-bodied anchor and an associated delivery system which enhances fixation of a micro anchor in a bone hole or tunnel, as well as improving suture lock within bone. Initially, the two bodies are separated by a length of an inner shaft of the delivery system. The proximal body is fixed on the inner shaft of the delivery system and cannot move relative to the handle until after insertion into the bone, when the delivery system is disengaged from the anchor. The distal body further includes expansion wings and/or other features for increasing suture lock within the bone hole.

22 Claims, 27 Drawing Sheets

Related U.S. Application Data filed on Dec. 6, 2016, provisional application No. 62/423,400, filed on Nov. 17, 2016, provisional application No. 62/369,997, filed on Aug. 2, 2016, provisional application No. 62/367,788, filed on Jul. 28, 2016.

(52) U.S. Cl.
CPC ........... *A61B 2017/0409* (2013.01); *A61B 2017/0412* (2013.01); *A61B 2017/0414* (2013.01); *A61B 2017/0422* (2013.01); *A61B 2017/0424* (2013.01); *A61B 2017/0429* (2013.01); *A61F 2002/0835* (2013.01); *A61F 2002/0852* (2013.01); *A61F 2002/0888* (2013.01); *A61F 2220/0016* (2013.01); *A61F 2250/0012* (2013.01)

(58) Field of Classification Search
CPC .... A61B 2017/0414; A61B 2017/0422; A61B 2017/0424; A61B 2017/0429; A61F 2/0811; A61F 2220/0016; A61F 2250/0012; A61F 2002/0817
USPC ........................................... 623/13.13
See application file for complete search history.

(56) References Cited

U.S. PATENT DOCUMENTS

| | | | |
|---|---|---|---|
| 2017/0172560 A1* | 6/2017 | Patel | A61B 17/0401 |
| 2017/0172562 A1* | 6/2017 | Lombardo | A61B 17/0401 |
| 2017/0290656 A1* | 10/2017 | Piccirillo | A61F 2/0805 |
| 2017/0304044 A1* | 10/2017 | Patel | A61B 17/0401 |

* cited by examiner

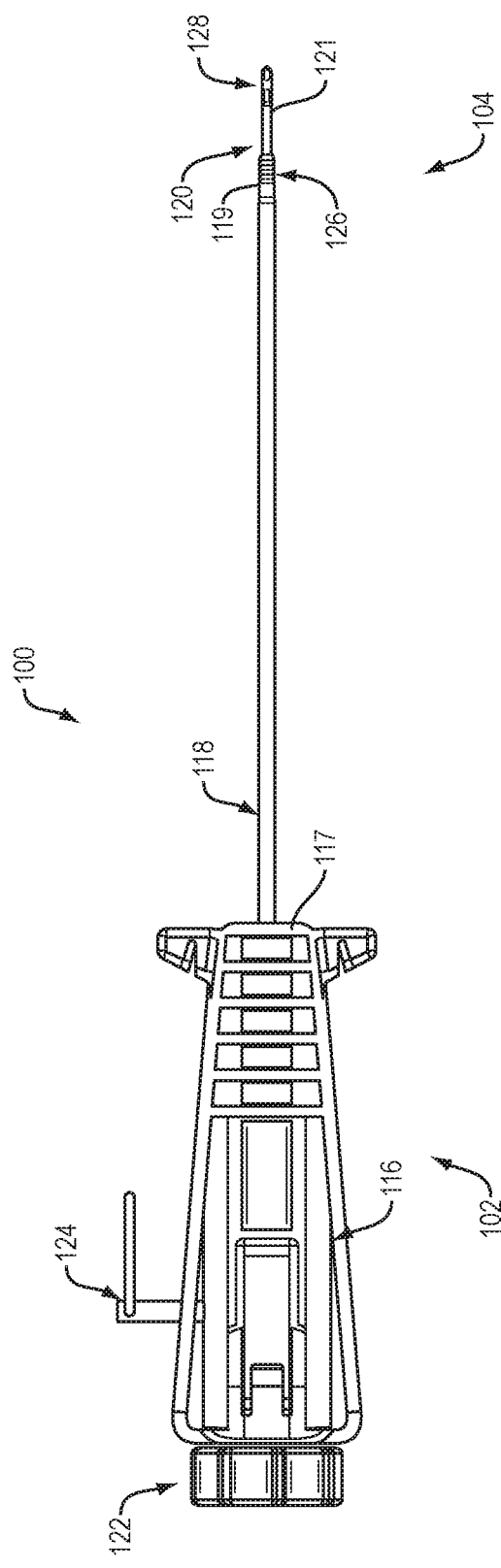
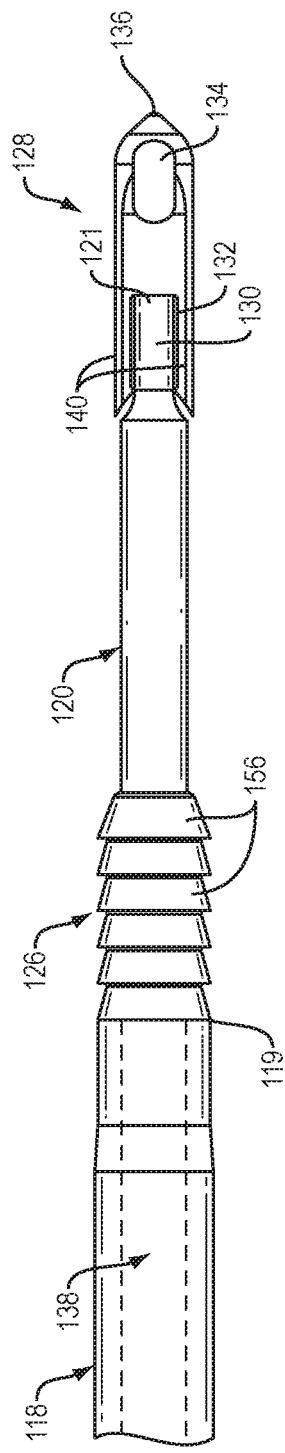
FIG. 1
FIG. 2

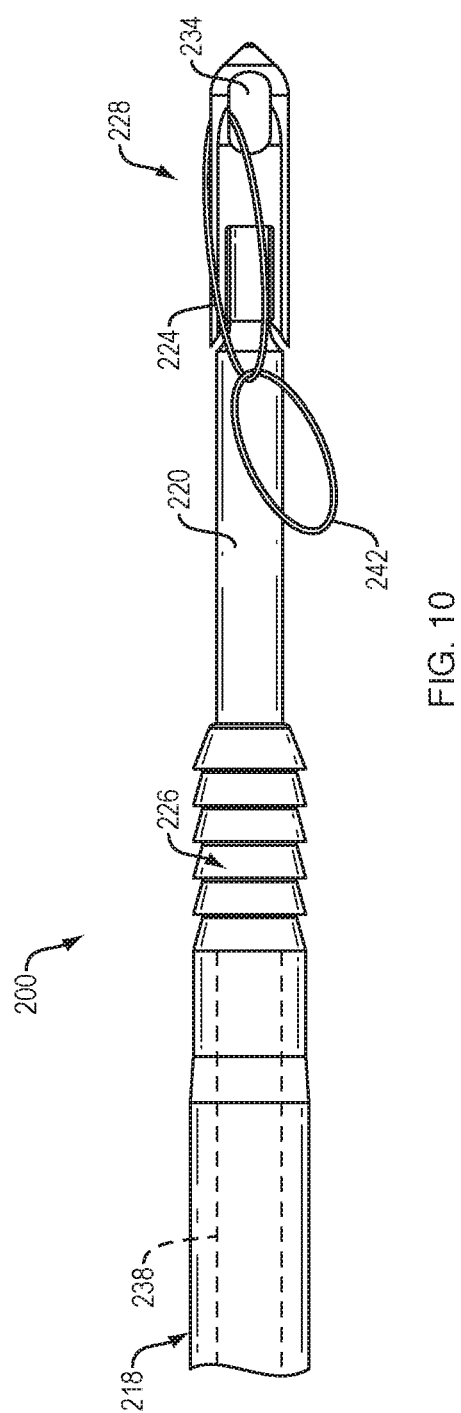

SUTURE SECURING ASSEMBLIES

CROSS-REFERENCE TO RELATED APPLICATIONS

This application is the U.S. national phase entry under 35 U.S.C. § 371 of International Application No. PCT/US2017/044004, filed Jul. 26, 2017, entitled SUTURE SECURING ASSEMBLIES, which in turn claims priority to and benefit of U.S. Provisional Application Nos. 62/367,788, filed Jul. 28, 2016, 62/369,997, filed Aug. 2, 2016, 62/423,400, filed Nov. 17, 2016, 62/430,461, filed Dec. 6, 2016 and 62/447,551, filed Jan. 18, 2017, the contents of which are incorporated herein by reference in their entirety for all purposes.

FIELD

This application relates to suture securing assemblies and, more particularly, to suture securing assemblies for knotless tissue repair.

BACKGROUND

Suture anchors are commonly employed to attach soft tissue, such as tendons or ligaments, to bone. For instance, in a rotator cuff repair in the shoulder, a suture is passed through a detached or damaged portion of a rotator cuff tendon and a suture anchor is implanted into the adjacent bone. By attaching the suture to the anchor, the tendon is pulled into contact with the bone to promote adhesion of the tendon to the bone. Such procedures are often performed arthroscopically through a narrow cannula. This reduces trauma to the patient but makes attachment of the suture to the anchor using a knot more difficult.

Knotless suture anchors have been developed which allow a surgeon to tension the suture to a desired degree and then affix the suture to the anchor without having to tie a knot. For example, a suture may be trapped between an inner member and outer member of an anchor in coaxial relation to one another, or the suture may be trapped between an anchor and the wall of a bone hole. Recently, however, surgeons have been moving towards the use of smaller anchors in surgical repairs, which may be less invasive and allow for more rapid patient healing. A problem arises with the user of smaller anchors, though, in that less surface area is available for frictional engagement with the surrounding bone. Thus, lower fixation strength is often observed in smaller anchors. In certain repairs, the fixation strength may be reduced to an unacceptably low level, jeopardizing the stability of the repair.

SUMMARY

Disclosed herein are suture seaming assemblies comprising two-bodied anchors and associated delivery systems which enhance fixation of micro anchors in a bone hole, as well as improve suture lock within bone. Initially, the two bodies are separated by a length of an inner shaft of the delivery system. The proximal body is fixed on the inner shaft and cannot move relative to the handle until after insertion into the bone, when the delivery system is disengaged from the anchor. The distal body further includes expansion wings and/or other features for increasing suture lock within the bone hole. Advantageously, the suture securing assemblies of this disclosure can be used with metal, plastic (PEEK), resorbable and biocomposite suture anchors.

Further examples of the suture securing assembly of this disclosure may include one or more of the following, in any suitable combination.

In examples, the suture securing assembly of this disclosure includes an inserter having an outer shaft having a proximal end, a distal end, and a longitudinal cannulation extending between the proximal and distal ends, and an inner shaft disposed within the cannulation such that a portion of the inner shaft extends from the distal end of the outer shaft. The inner shaft is axially moveable relative to the outer shaft. The suture securing assembly also includes an anchor having a cannulated proximal body disposed on the inner shaft of the inserter near the distal end of the outer shaft and a distal body disposed on the inner shaft near a distal end of the inner shaft. The distal body has a transverse through hole for passage of a suture. The distal body is moveable by the inner shaft in a proximal direction relative to the proximal body, but the proximal body is prevented by a portion of the inserter from moving in a distal direction relative to the distal body.

In further examples, the suture securing assembly includes a handle attached to the proximal end of the outer shaft. The handle has a rotatable knob threadingly attached to the handle, the knob being attached to the inner shaft for retracting the inner shaft relative to the outer shaft. At least one of the proximal body and the distal body is made from any combination of metal, polymer, bioabsorbable, or biocomposite material. A cavity of the distal body defines a first locking feature and the inner shaft defines a second locking feature for mechanical engagement with the first locking feature. In examples, the first locking feature is a first plurality of threads formed on an inner surface of the cavity, and the second locking feature is a second plurality of threads formed on an outer surface of the inner shaft, the second plurality of threads being configured to mate with the first plurality of threads. In other examples, the first locking feature is a hole formed in the cavity and the second locking feature is a plurality of barbs on an outer surface of the inner shaft, the hole being configured to press over the barbs. In yet further examples, the engagement between the first locking feature and the second locking feature allows articulation of the distal body relative to the proximal body about any axis.

In still further examples, the distal body comprises expansion wings for engagement with a prepared bone hole. In examples, the suture securing assembly includes a flexible strand in the form of a closed loop extending through the through hole, the flexible strand for coupling to a suture. The flexible strand is made of at least one of suture, plastic and malleable metal. In examples, a surface of the distal body between the proximal end and the through hole comprises a plurality of passive wings, the passive wings being outwardly flexible upon insertion into bone. The passive wings are comprised of one of PEEK, other plastics, and metals. In examples, the distal body and/or the proximal body has features for allowing rotation of the distal body relative to the proximal body in a first direction, but preventing rotation of the distal body relative to the proximal body in a second direction.

In examples, the method of securing a suture in a bone hole of this disclosure includes passing a length of suture through a through hole of a distal body of an anchor. The distal body is placed at the bottom of a prepared bone hole, a proximal body of the anchor being separated by a distance from the distal body such that the proximal body is located outside of the bone hole. The length of suture is tensioned and a portion of the proximal body is inserted into the bone hole such that legs of the length of suture are fixed between the proximal body and the bone hole. The distance between the proximal body and the distal body are unchanged. The distal body is retracted toward the proximal body, creating suture slack in the bone hole. The distal body and the proximal body are driven together into the bone hole such that the suture slack in the bone hole is removed. In further examples, the distal body is spaced apart from the proximal body of the anchor along a length of an inner shaft of an inserter, and retracting the distal body toward the proximal body includes retracting the inner shaft relative to a handle of the inserter. When driving the distal body and the proximal body together into the bone hole, there is no relative motion between the distal body and the proximal body.

In other examples, the method of securing a suture in a bone hole of this disclosure includes passing a length of suture through a through hole of a distal body of an anchor. The anchor has a cannulated proximal body disposed on an inner shaft of an inserter near a distal end of an outer shaft of the inserter. The distal body is disposed on the inner shaft near a distal end of the inner shaft and has radially expanding wings at a proximal end. The distal body is approximated to a hole formed in bone. The length of suture is tensioned and the proximal body and the distal body are inserted into the bone hole. The distance between the proximal body and the distal body are unchanged. The distal body is retracted toward the proximal body by retracting the inner shaft relative to a handle of the inserter such that the wings engage the proximal body, causing the wings to radially expand. The inner shaft is further retracted such that the proximal body and the distal body are disengaged from the inner shaft. Thus, the length of suture is compressed between the distal body and the bone hole.

In further examples, passing the length of suture through the through hole of the distal body includes passing the length of suture with a suture threader. In examples, the inner shaft is coupled to a knob of a handle, and retraction of the inner shaft includes rotating the knob of the handle. In examples, the handle has a first set of features for engagement with a second set of features on the knob, the engagement providing audible and tactile feedback to a user. In examples, the handle includes a stop feature for limiting retraction of the inner shaft relative to the handle. In examples, the method further includes passing the length of suture through tissue.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIG. 1 is an illustration of an exemplary suture securing assembly of this disclosure;

FIG. 2 is a detailed, cutaway view of the distal components of the suture securing assembly of FIG. 1;

FIG. 10 is an illustration of an alternative suture securing assembly of this disclosure;

DETAILED DESCRIPTION

Figure 3:
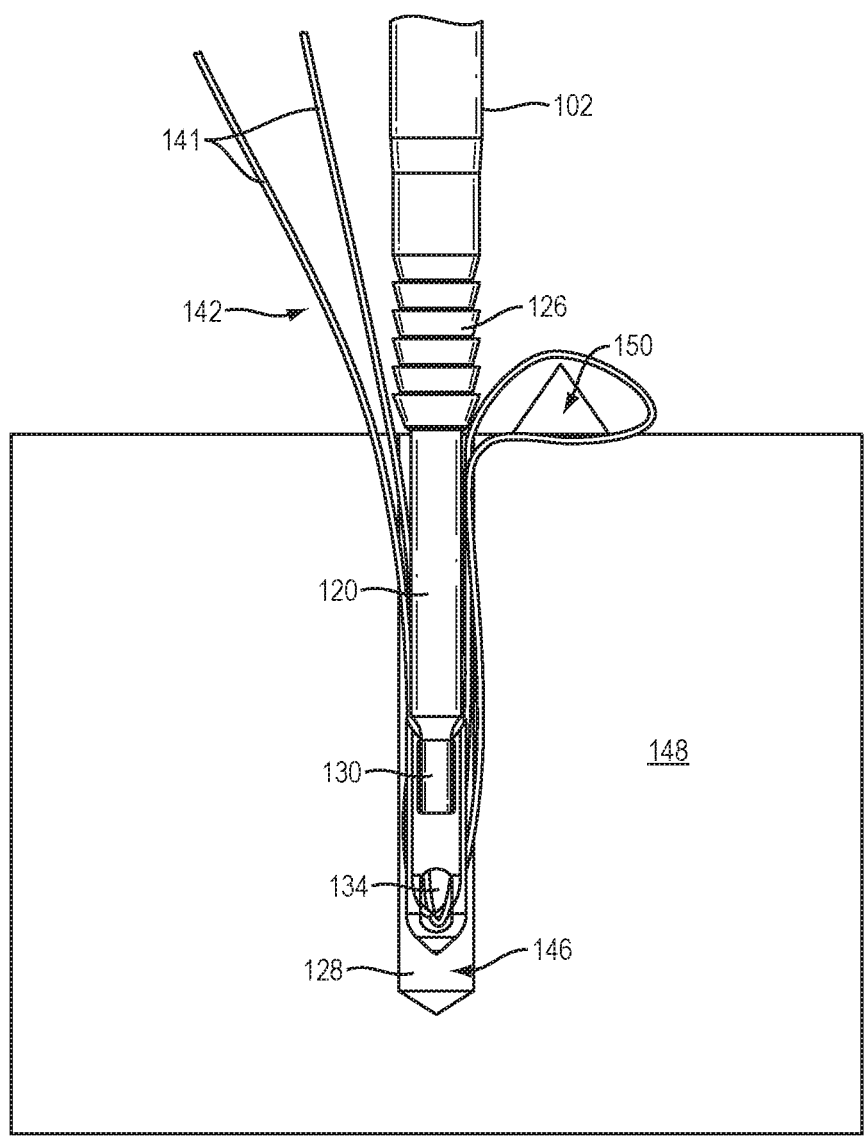
FIGS. 3-8B illustrate the use of the suture securing assembly of FIG. 1 during a soft tissue repair.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

FIG. 1 depicts an exemplary suture securing assembly 100 according to the present disclosure. The suture securing assembly 100 generally comprises an inserter 102 and a two-bodied anchor 104. The inserter 102 comprises a handle 116, an outer shaft 118 fixedly attached to the distal end 117 of the handle 116, and an inner shaft 120 extending from the distal end 119 of the outer shaft 118. A knob 122 is threadingly coupled to the handle 116 and is rotatable independent of the handle 116. The inner shaft 120 extends through a channel 138 (FIG. 2) in the outer shaft 118 and is fixedly attached to the knob 122 such that it is axially and/or rotationally moveable independent of the outer shaft 118 by rotation of the knob 122. It is also contemplated by this disclosure that the translation of the inner shaft 120 relative to the outer shaft 118 could be accomplished by a prismatic joint, linkage or other such mechanism which could provide the required movement. The inserter 102 may further include a locking pin 124 extending through a wall of the handle 116, the function of which will be further described below.

Still referring to FIG. 1, the anchor 104 comprises a cannulated proximal anchor body 126 disposed on the inner shaft 120 near the distal end 119 of the outer shaft 118. The anchor 104 also comprises a distal anchor body 128 disposed on the inner shaft 120 near a distal end 121 of the inner shaft 120. Either or both of the proximal anchor body 126 and the distal anchor body 128 can be sized appropriately for instability or rotator cuff repair. A diameter of the distal anchor body 128 is selected to be smaller than a diameter of the proximal anchor body 126, and also smaller than a diameter of a prepared bone hole. A diameter of the proximal anchor body 126 is selected to be the same as or slightly larger than the diameter of the prepared bone hole. For example, a diameter of the proximal anchor body may be about 2.7 mm and a diameter of the prepared bone hole may be about 2.2 mm.

Either or both of the proximal anchor body 126 and the distal anchor body 128 can be made from any combination of metal, PEEK, bioabsorbable, or biocomposite material. For example, the proximal anchor body 126 and/or the distal anchor body 128 may be partially or entirely formed from a formulation of poly(lactic-co-glycolic) acid (PLGA), β-Tricalcium phosphate (β-TCP) and calcium sulfate, poly-L-lactic acid-hydroxyapatite (PLLA-HA), poly-D-lactide (PDLA), polyether ether ketone (PEEK) or variants thereof. Biocomposite examples made from a combination of PLGA, β-TCP, and calcium sulfate are absorbable by the body, which is beneficial to natural healing. An example formulation of PLGA, β-TCP, and calcium sulfate is described in U.S. Pat. No. 8,545,866, the entirety of which is herein incorporated by reference. A copolymer of polyglycolic acid (PGA) and polytrimethylene carbonate (TMC) is another example of a bioabsorbable material. In examples, the distal anchor body 128 could be an all-suture anchor. Other commonly used materials that are capable of providing the strength needed to set the anchors into position and to hold the suture and tissue in position while bone-to-tissue ingrowth occurs are also contemplated by this disclosure.

A detailed view of the outer shaft 118, the inner shaft 120, the proximal anchor body 126 and the distal anchor body 128 is shown in FIG. 2. The inner shaft 120 is slidably disposed in, and extends from, the channel 138 in the outer shaft 118. The proximal anchor body 126 may comprise barbs 156 or other surface features which help it anchor into bone. In examples, the proximal anchor body 126 may be locked into position relative to the outer shaft 118 by a press fit (i.e., friction) between the proximal anchor body 126 and the inner shaft 120, or by a threaded interface with the inner shaft 20, such that the proximal anchor body 126 resists proximal movement under normal use conditions. The locking mechanism, which may be a break-away feature, could also be located on the outer shaft 118.

Still referring to FIG. 2, the distal end 121 of the inner shaft 120 comprises a threaded portion 130 for mating with a threaded interior cavity 132 of the distal anchor body 128. The cavity 132 extends from a proximal end of the distal anchor body 128 to a region proximal to a transverse through hole 134. The through hole 134 is configured for passage of a suture which may then be placed at the bottom of a bone hole. It is also contemplated by this disclosure that the distal anchor body 128 has a fork or other suitable feature that allows it to place a suture at the bottom of a bone hole. In FIG. 2, the distal anchor body 128 also has a pointed tip 136 for being driven into bone. Optionally, the distal anchor body 128 may comprise expansion wings 140, described in further detail below. It is also contemplated by this disclosure that the distal anchor body 128 can include asymmetrical surface features that cause it to toggle in the bone hole during insertion to create increased fixation loads.

FIGS. 3-8B illustrate the use of the suture securing assembly 100 of FIG. 1. In FIGS. 3-8B, the suture securing assembly 100 is used for a shoulder instability (labral) repair. However, it is contemplated by this disclosure that the suture securing assembly 100 could be adapted or scaled for other types of surgical repair.

In FIG. 3, a length of suture 142 is first passed through a section of tissue 150, such as a labrum or rotator cuff tendon. It is then passed through the through hole 134 of the distal anchor body 128 such that ends of the suture 142 enter and exit from the same location of the bone hole 146. The bone hole 146 is formed in an adjacent bone 148 at a desired location for placement of the anchor 104. The distal anchor body 128, which is threaded to the threaded portion 130 of the inner shaft 120, is positioned at the bottom of the bone hole 146, while the proximal anchor body 126 is not in contact with the bone 148. Thus, the proximal anchor body 126 and the distal anchor body 128 are separated by approximately the length of the bone hole 146. At this point, the suture 142 can still be tensioned to provide the desired position of and tension upon the tissue 150, because the distal anchor body 128 is sized to allow clearance in the bone hole 146 for the suture 142 to slide. Notably, the only motion allowed by the inserter 102 at this step is rotation of the knob 122 (FIG. 1).

Figure 4:
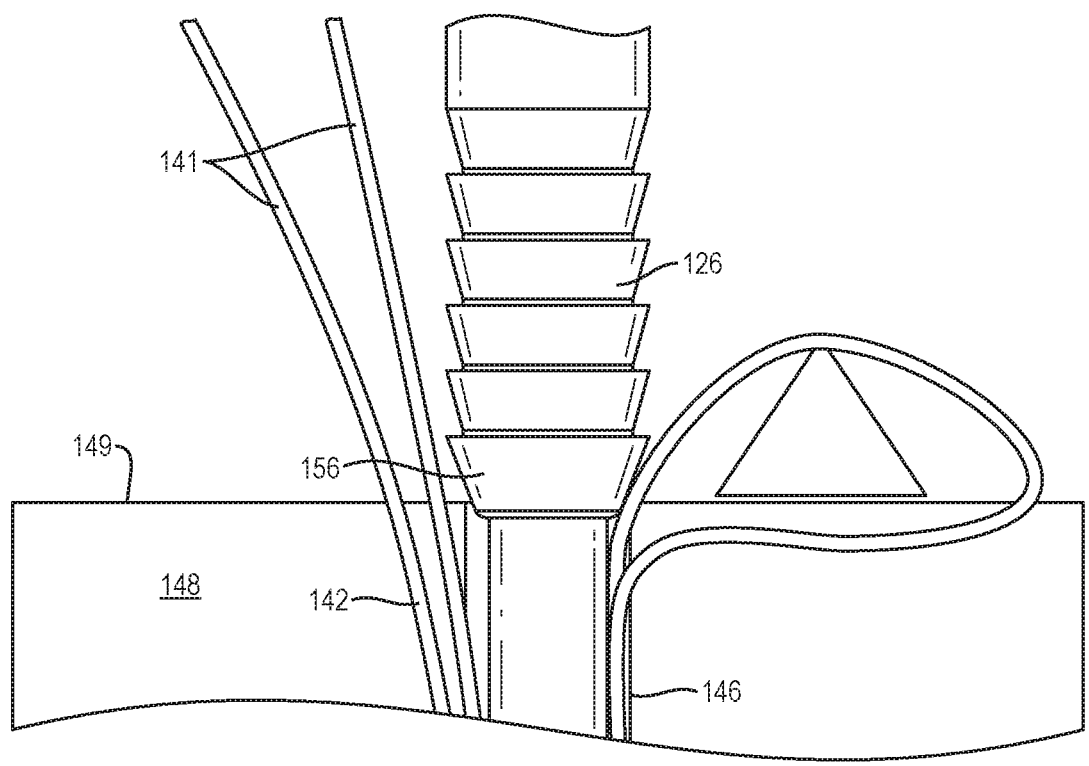

As shown in FIG. 4, once the desired tension on the tissue has been achieved, the proximal anchor body 126 is approximated to the cortical surface 149 of the bone 148, where it locks the length of suture 142 in the bone hole 146. This is accomplished by applying a light downward pressure, either manually or by tapping on the handle 116 (FIG. 1) with a hammer, such that the first barb 156 of the proximal anchor body 126 is beneath the cortical surface 149 of the bone 148. When this occurs, the legs 141 of the suture 142 are impinged between the proximal anchor body 126 and the opening of the bone hole 146 such that the length of the suture 142 from entry to exit of the bone hole 146 may not change. Notably, no relative motion between the proximal anchor body 126 and distal anchor body 128 has occurred at this point.

Figure 5B:
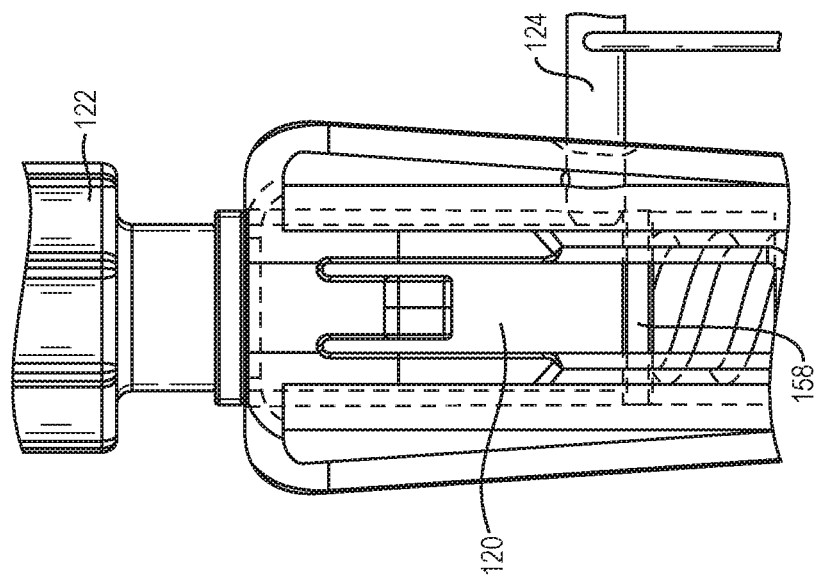
Figure 5A:
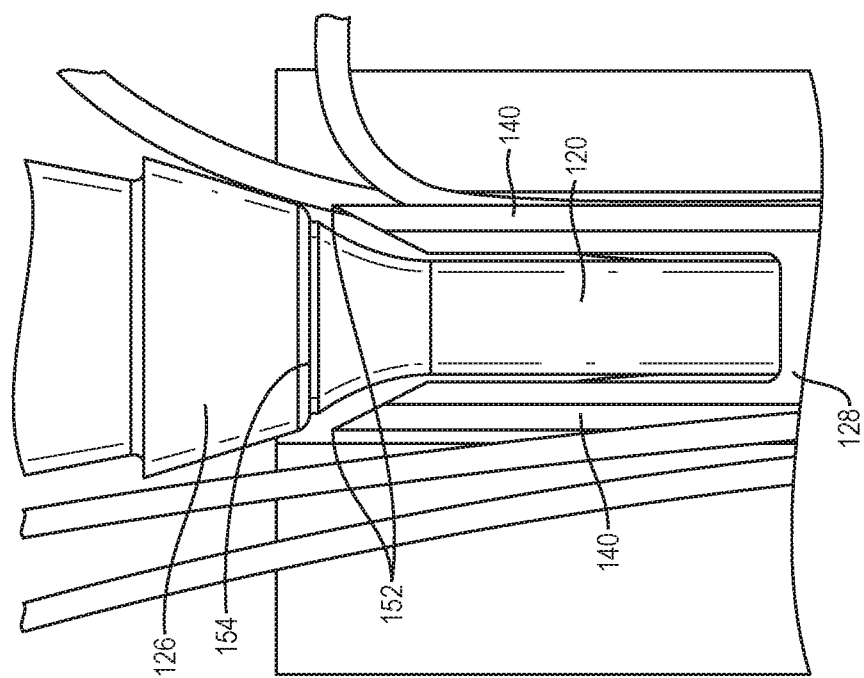

As shown in FIG. 5A, the distal anchor body 128 is next retracted toward the proximal anchor body 126. This is accomplished by rotation of the knob 122 (FIG. 5B) which rotates and retracts the inner shall 120, which in turn rotates and retracts the distal anchor body 128. As shown in FIG. 5B, the inner shaft 120, near its attachment to the knob 122, comprises an area of increased diameter 158 which, as the inner shaft 120 is rotated and retracted, comes to rest on the locking pin 124. The locking pin 124 thus provides a hard stop for this initial retraction of the inner shaft 120. At this point, the distal anchor body 128 has retracted such that the proximal edges 152 of the wings 140 are nearly coplanar with the distal angled face 154 of the proximal anchor body 126. The locking of this position is critical, for any further retraction of the distal anchor body 128 would cause premature deployment of the wings 140.

Figure 6:
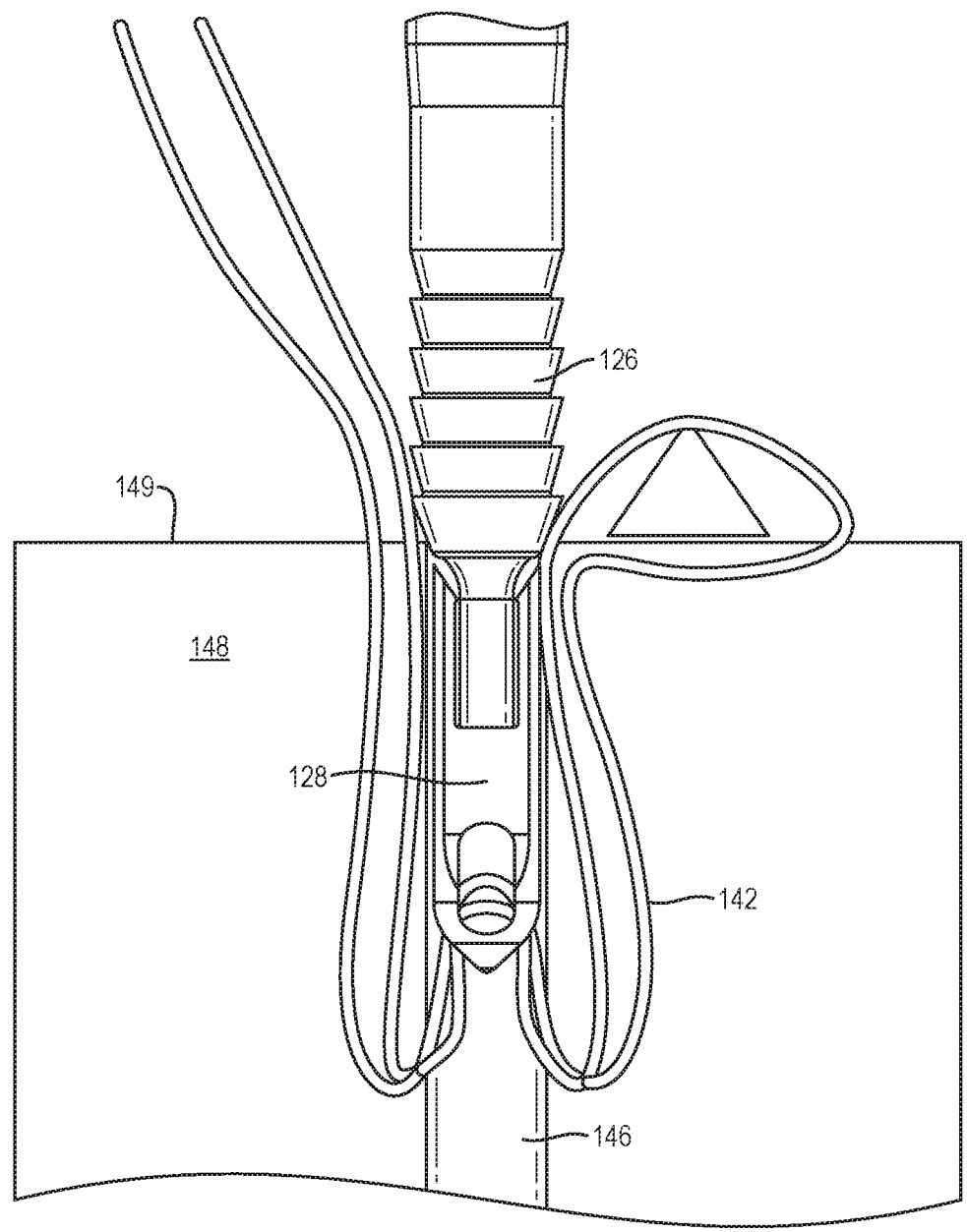

In FIG. 6, the proximal anchor body 126 is shown as still being locked into place relative to the bone hole 146. As retraction of the distal anchor body 128 occurs, slack in the suture 142 is created in the bone tunnel 146. As stated above, the length of the suture 142 in the bone tunnel 146 has remained constant, since the proximal anchor body 126 is locking the suture 142 into place at the cortical surface 149 of the bone 148.

Figure 7:
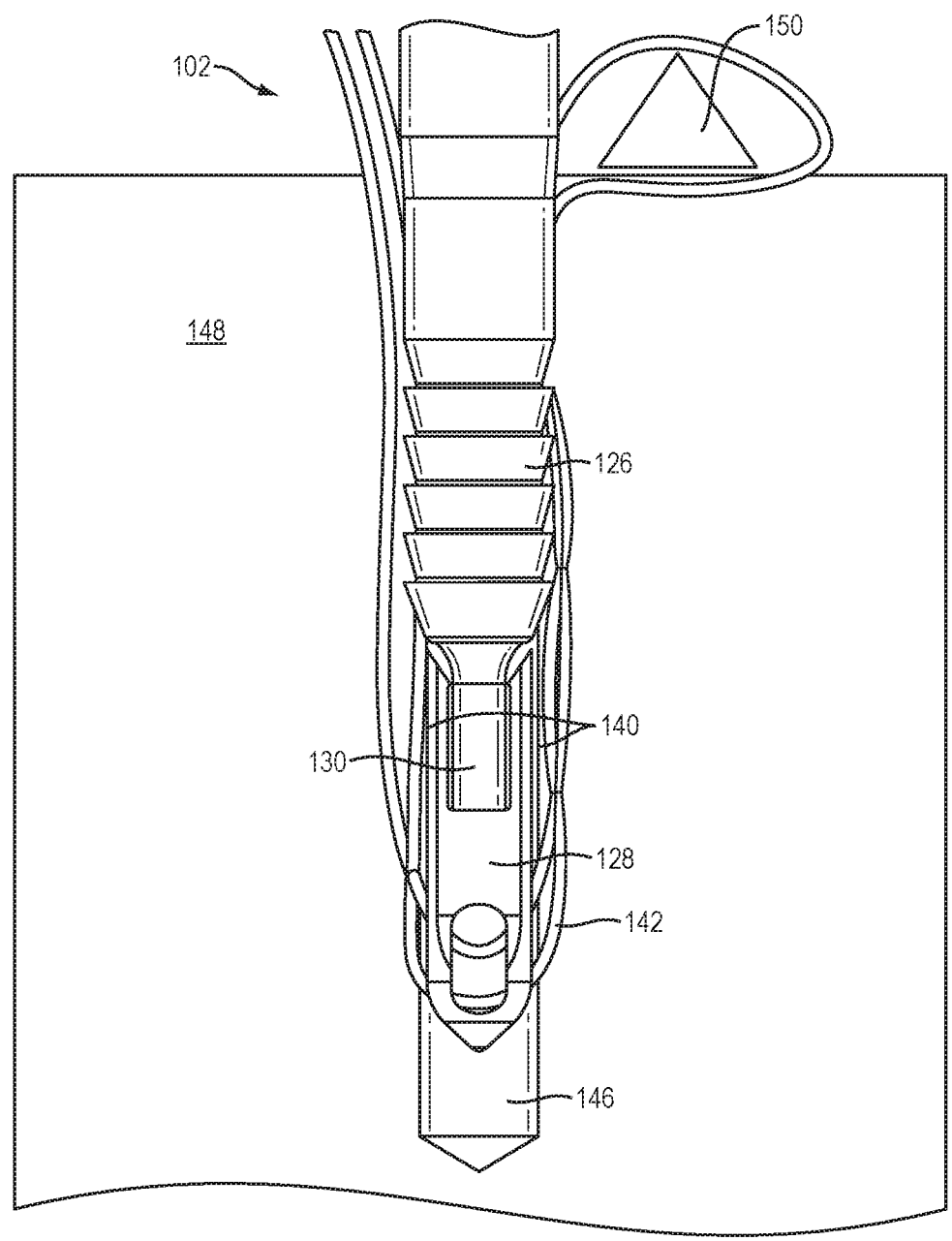

As shown in FIG. 7, the inserter 102 is then impacted (for example, with a hammer) toward the bone 148 such that both the proximal anchor body 126 and the distal anchor body 128 are driven distally in the bone hole 146 together. In other words, there is no relative motion between the proximal anchor body 126 and the distal anchor body 128. The slack in the length of the suture 142 inside the bone hole 146 is removed as the proximal anchor body 126 and distal anchor body 128 are driven into place, and no additional tension is applied to the tissue 150. In the threaded interface between the distal anchor body 128 and the threaded portion 130 of the inner shaft 120, the pitch of the thread is selected so that the proximal anchor body 126 and the distal anchor body 128 do not move relative to one another. This prevents premature deployment of the wings 140 and ensures that the proximal anchor body 126 and distal anchor body 128 are moving in lockstep. At this point, the slack in the length of the suture 142 in the bone hole 146 has been removed, appropriate tension has been maintained on the tissue 150, and the proximal anchor body 126 and distal anchor body 128 have been driven into the bone 148 in order to lock the desired tension on the tissue 150.

Figure 8B:
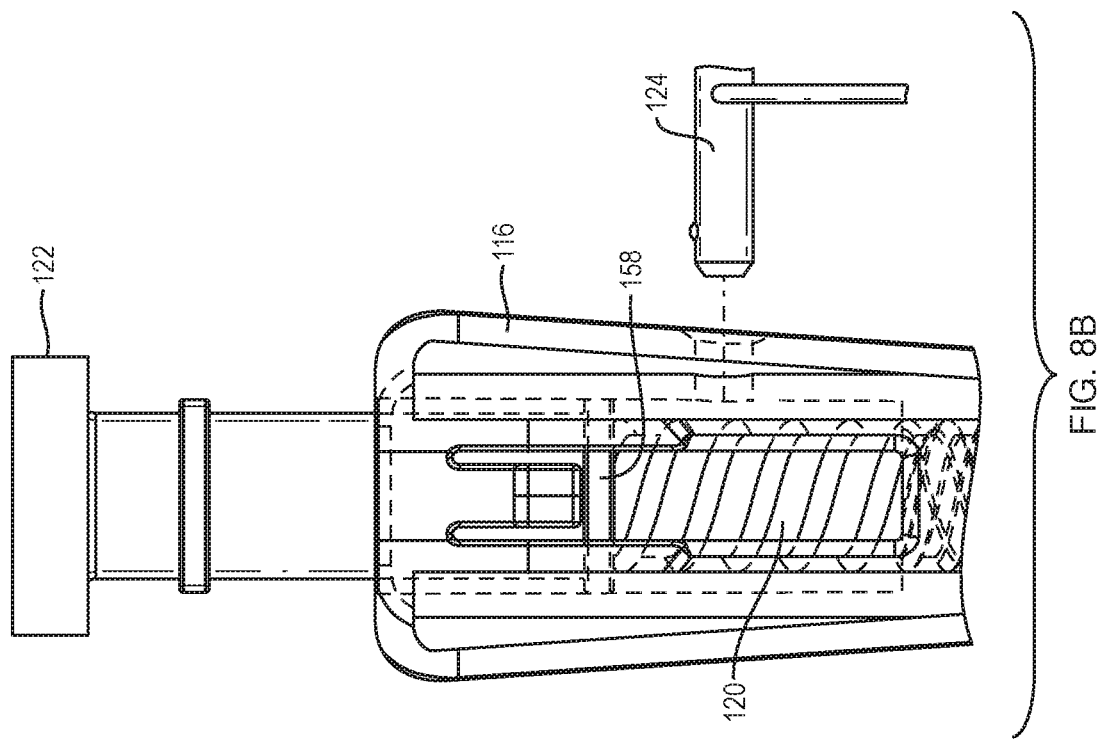
Figure 8A:
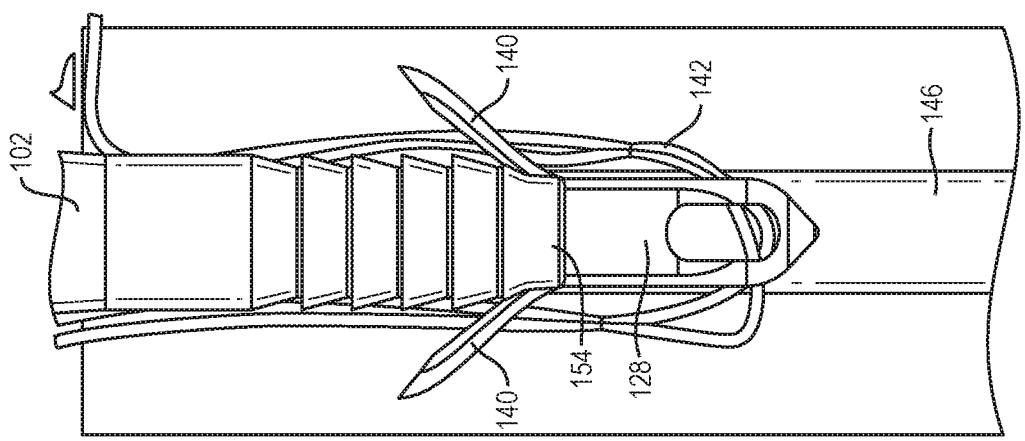

The final step of the method of this disclosure is shown in FIGS. 8A and 8B. FIG. 8A illustrates a second retraction of the distal anchor body 128. This is accomplished by first removing the locking pin 124 from the handle 116, as shown in FIG. 8B. Removing the locking pin 124 allows the knob 122 to be turned further, since the area of increased diameter 158 on the inner shaft 120 is no longer stopped by the locking pin 124 and the inner shaft 120 can continue to move in a proximal direction. It is contemplated by this disclosure that the locking action may also be completed by any other removable member, or a sliding member that allows further rotation of the knob 122 but does not disengage completely from the handle 116. Rotation of the knob 122 also results in additional retraction and rotation of the inner shaft 120 and distal anchor body 128. As the distal anchor body 128 retracts toward the proximal anchor body 126, the wings 140 of the distal anchor body 128 encounter the distal angled face 154 on the proximal anchor body 126, causing the wings 140 to be forced outwards, advantageously providing additional fixation force within the bone hole 146. Once the wings 140 are expanded, it is contemplated by this disclosure that the distal anchor body 128 could contain a feature which locks it to the proximal anchor body 126 once they are in contact. The inner shaft 120 continues to rotate and retract until it forces the distal anchor body 128 off of it. Simultaneously, retraction of the inner shaft 120 strips the threads or otherwise disengages the locking feature between the proximal anchor body 126 and the inner shaft 20, forcing the proximal anchor body 126 off of the inner shaft 120 as well. This results in the complete disengagement of the proximal anchor body 126 and the distal anchor body 128 from the inserter 102. The inserter 102 can then be removed from the repair site, leaving the proximal anchor body 126, the distal anchor body 128, and the suture 142 lodged in the bone hole 146.

Figure 9:
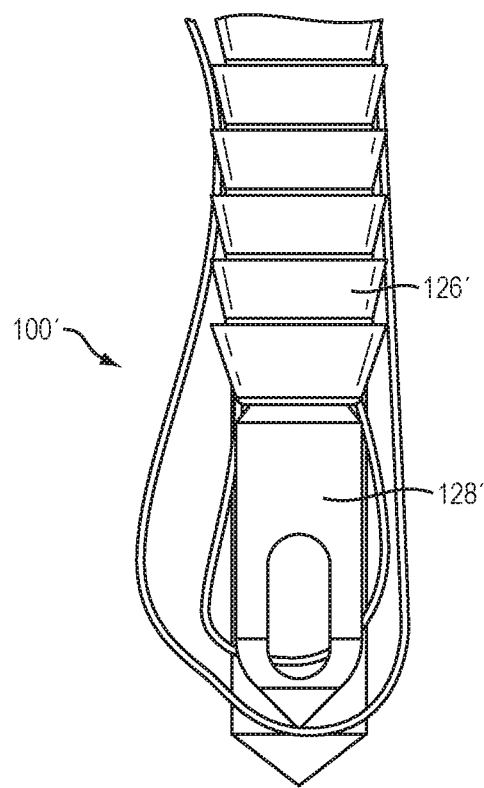
FIG. 9 is an alternative example of the anchor of FIG. 1.

An alternative example of a suture securing assembly 100' having a proximal anchor body 126' and a distal anchor body 128' is shown in FIG. 9. The suture securing assembly 100' is substantially similar to the suture securing assembly 100 except that, in this example, the distal anchor body 128' does not have expansion wings 140. Accordingly, the locking pin 124 of the handle 118 (FIG. 1) would not be necessary since there would be no need for a two-step retraction process.

The above disclosure relates to knotless suture securing assemblies. However, a surgeon may sometimes find it more convenient to use the suture securing assembly together with a knotted suture. It would therefore be desirable for a surgeon to have the ability to easily convert the knotless suture securing assembly for use with a knotted suture.

FIG. 10 illustrates another example of a suture securing assembly 200 of this disclosure. The suture securing assembly 200 is substantially similar to the suture securing assembly 100 of FIG. 2 except as described below. In FIG. 10, the through hole 234 of the distal anchor body 228 is configured for passage of at least one transfer eyelet 224. The transfer eyelet 224 is comprised of any length or geometry of flexible material, which may be any resorbable or non-resorbable material, such as suture, plastic or malleable metal (e.g. Nitinol), formed into a closed loop. One or more lengths of repair suture 242 are weaved through or otherwise attached to a portion of the transfer eyelet 224. Advantageously, the transfer eyelet 224 of this disclosure allows the suture anchor system 200 to be used in both knotted and knotless suture constructs.

Figure 11A:
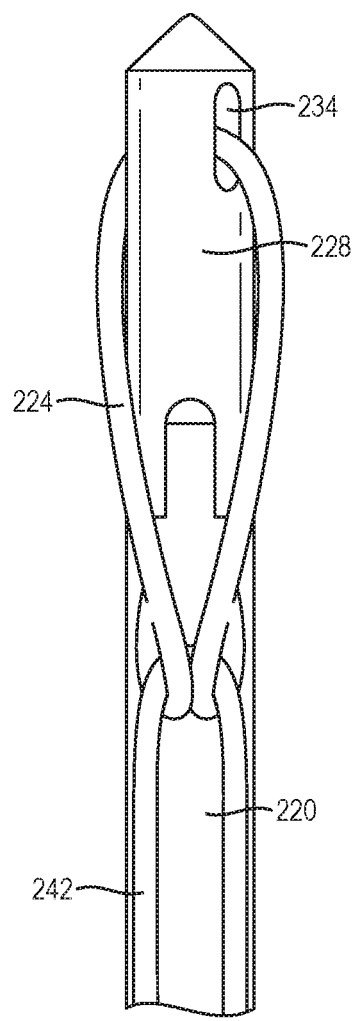
FIGS. 11A-E illustrate the use of the suture securing assembly of FIG. 10 during a soft tissue repair.
Figure 11B:
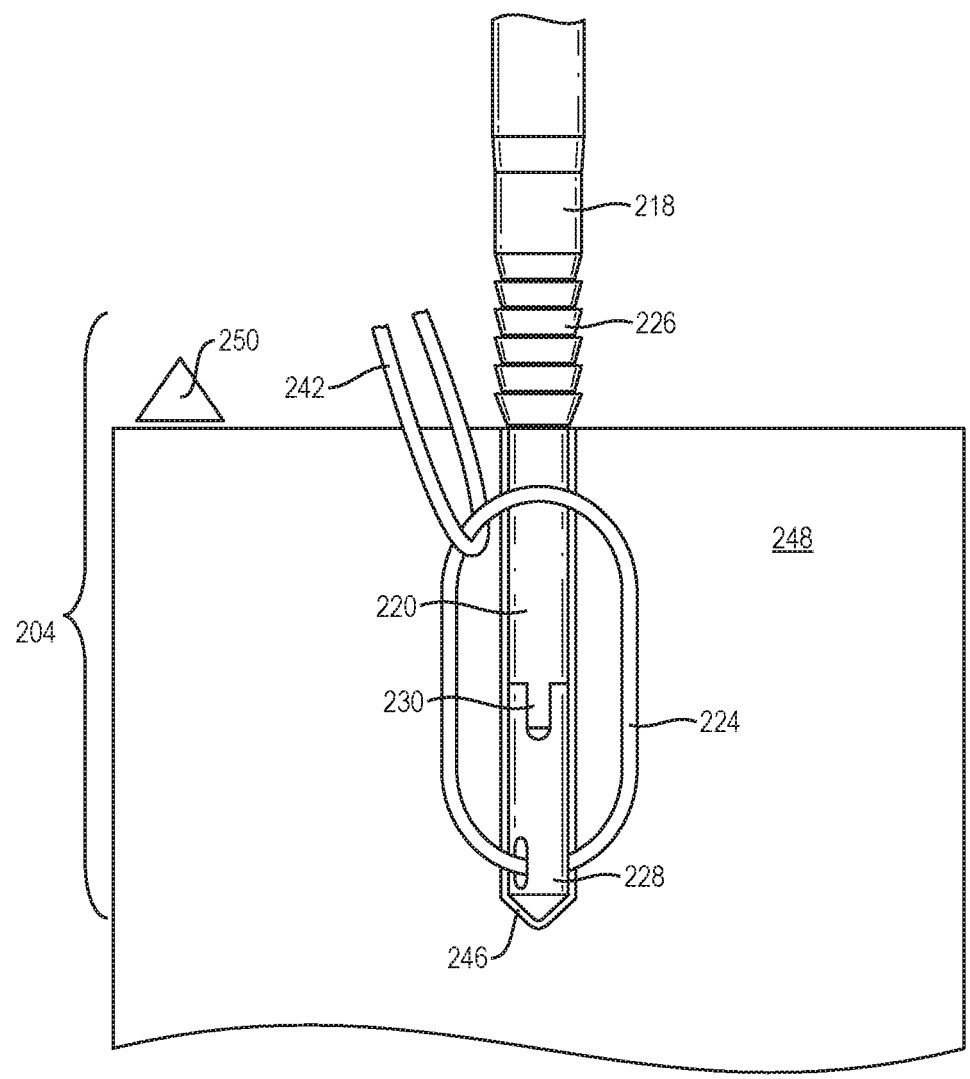
Figure 11C:
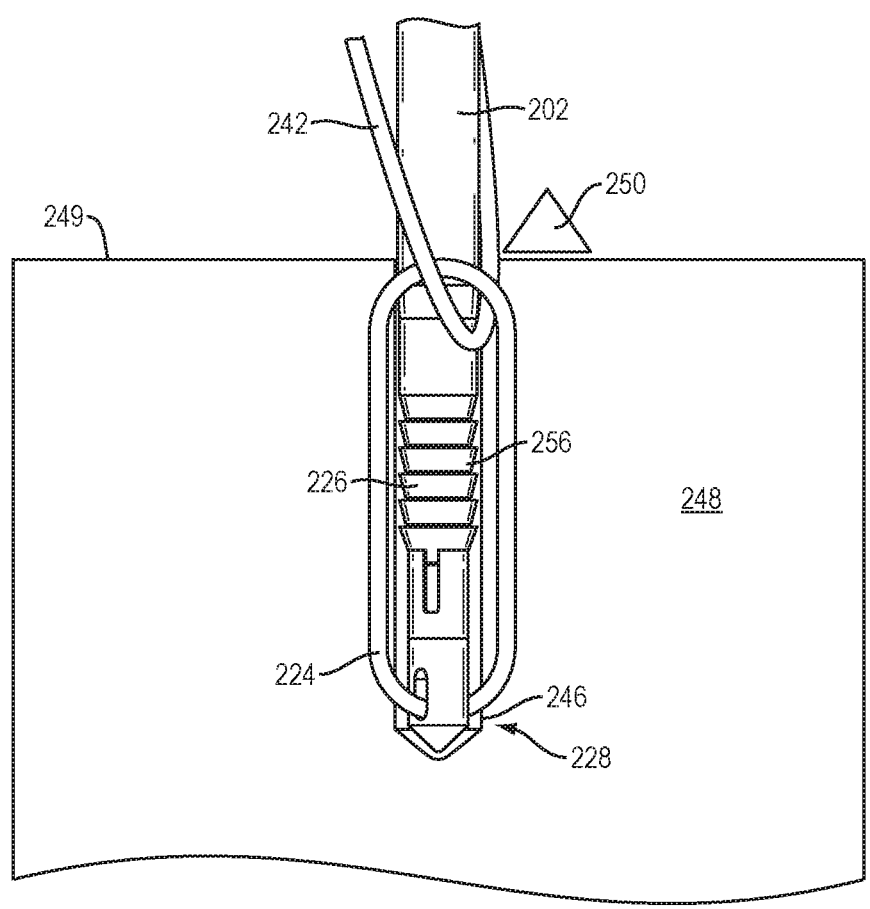

FIGS. 11A-C illustrate a method of using of the suture securing assembly 200 of FIG. 10 in a soft tissue repair. For example, the soft tissue repair may be a shoulder instability (labral) repair. However, it is contemplated by this disclosure that the suture securing assembly 200 of this disclosure could be adapted or scaled for other types of surgical repair.

Turning now to FIG. 11A, the distal anchor body 228 is shown as mounted to the inner shaft 220, with a transfer eyelet 224 extending through the through hole 234 therein. To begin the repair, a repair suture 242 is first woven through or otherwise attached to the transfer eyelet 224. In FIG. 11B, a bone hole 246 is formed in a bone 248 at a desired location for placement of the anchor 204. The distal anchor body 228, which is threaded to the threaded portion 230 of the inner shaft 220, is positioned at the bottom of the bone hole 246, while the proximal anchor body 226 is outside of the bone hole 246. Advantageously, adjustment of the transfer eyelet 224 and the repair suture 242 to provide the desired position is still possible at this point because the distal anchor body 228 is sized to allow clearance in the bone hole 246 for both the transfer eyelet 224 and the repair suture 242 to slide.

Next, as shown in FIG. 11C, once the desired placement of the transfer eyelet 224 and the repair suture 242 is achieved, the proximal anchor body 226 is inserted into the bone 248. This is accomplished, for example, by applying a light downward pressure, either manually or by tapping on the inserter 202 with a hammer, such that the first barb 256 of the proximal anchor body 226 is beneath the cortical surface 249 of the bone 248. As the proximal anchor body 226 is inserted into bone 248, there is no relative motion between the proximal anchor body 226 and distal anchor body 228. The distal anchor body 228 is then retracted toward the proximal anchor body 226. This is achieved by rotation of the knob 222 (FIG. 1), or by other actuation means within the handle, which rotates and retracts the inner shaft 220 of the inserter 202, which in turn rotates and retracts the distal anchor body 228 until the distal anchor body 228 and proximal anchor body 226 abut one another. The inserter 202 is then impacted (for example, with a hammer) toward the bone 248 such that both the proximal anchor body 226 and the distal anchor body 228 are driven distally in the bone hole 246 together, with no relative movement therebetween. The inner shaft 220 then continues to be rotated and retracted until it forces the distal anchor body 228 off of it. Simultaneously, retraction of the inner shaft 220 strips the threads or otherwise disengages the locking feature between the proximal anchor body 226 and the inner shaft 220, forcing the proximal anchor body 226 off of the inner shaft 220 as well. This results in the complete disengagement of the proximal anchor body 226 and the distal anchor body 228 from the inserter 202.

Figure 11D:
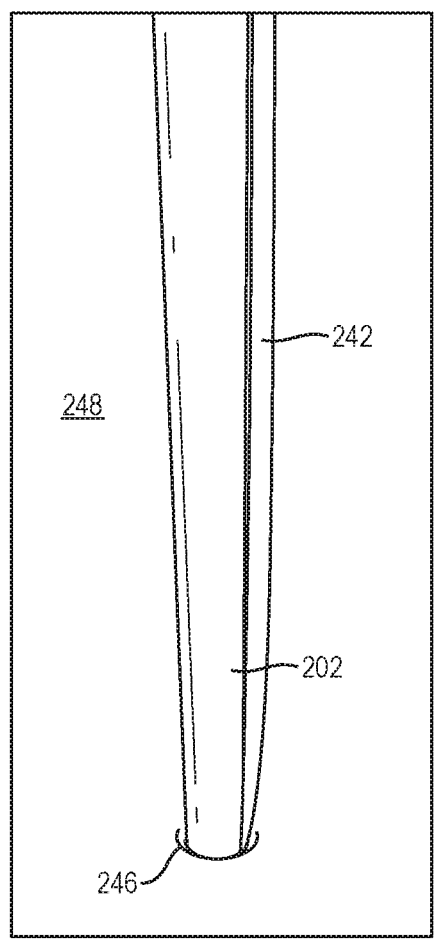
Figure 11E:
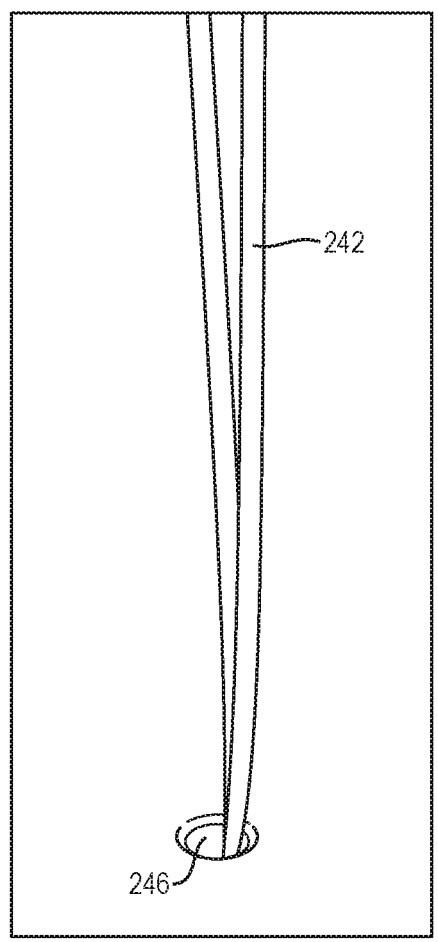

FIG. 11D shows the inserter 202 still inserted into bone 248, with the repair suture 242 extending from the bone hole 246. It should be noted that a length of the transfer eyelet 224 is selected to leave some amount of the transfer eyelet 224 proud of the proximal anchor body 226 such that the repair suture 242 is not impinged between the proximal anchor body 226 and the bone hole 246 and is thus still free to slide relative to the transfer eyelet 224. As illustrated in FIG. 11E, the inserter 202 can then be removed from the repair site, leaving the repair suture 242 extending from the bone hole 246. The repair suture 242 can then be passed through soft tissue. After passing the repair suture 242 through the soft tissue, knots can be tied in the repair suture 242 and the repair can be completed.

It should be noted that use of the transfer eyelet 224 is not limited to the suture securing assembly 200 described above. The transfer eyelet 224 could also be used with other two-bodied anchor assemblies. Non-limiting examples of such two-bodied anchor assemblies are disclosed in International Publication No. WO 2015/134872 to Smith & Nephew, Inc., the entire contents of which are incorporated herein by reference. The transfer eyelet 224 could also be used with the suture securing assemblies 300, 400, 500 and 600 of this disclosure, as further described below.

Figure 12A:
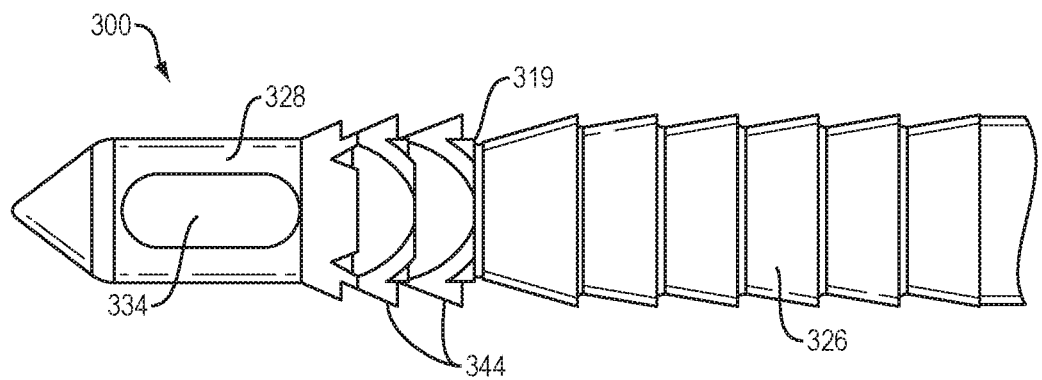
FIGS. 12A-F illustrate an alternative suture securing assembly of this disclosure and method of use.

FIG. 12A illustrates yet another example of a suture securing assembly 300 of this disclosure in which the distal anchor body 328 is rotatable relative to the proximal anchor body 326. The suture securing assembly 300 is substantially similar to the suture anchor assemblies 100, 200 except as described below. As shown in FIG. 12A, the surface of the distal anchor body 328 between the through hole 334 and the proximal end 319 of the distal anchor body 328 comprises a plurality of proximally-extending, passive wings 344 (three as shown, although more or fewer than three wings are contemplated by this disclosure). The wings 344 may be made of any material that allows the wings 344 to flex without fracture, such as PEEK, other plastics, or any metals.

Figure 12B:
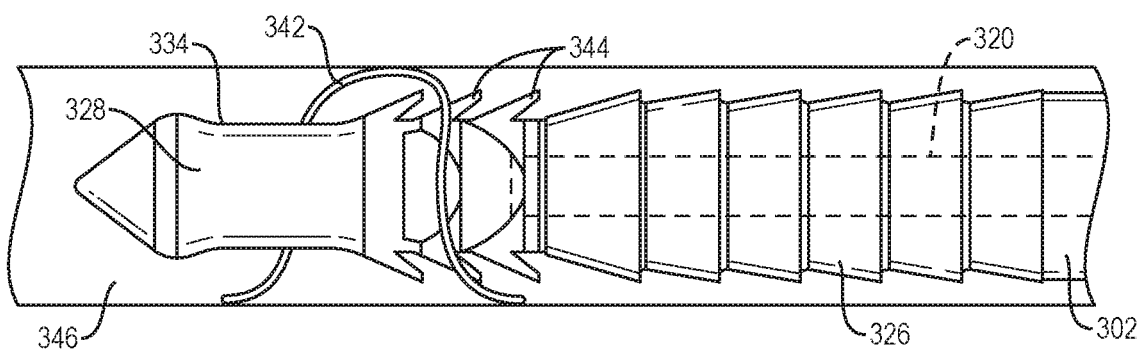
Figure 12C:
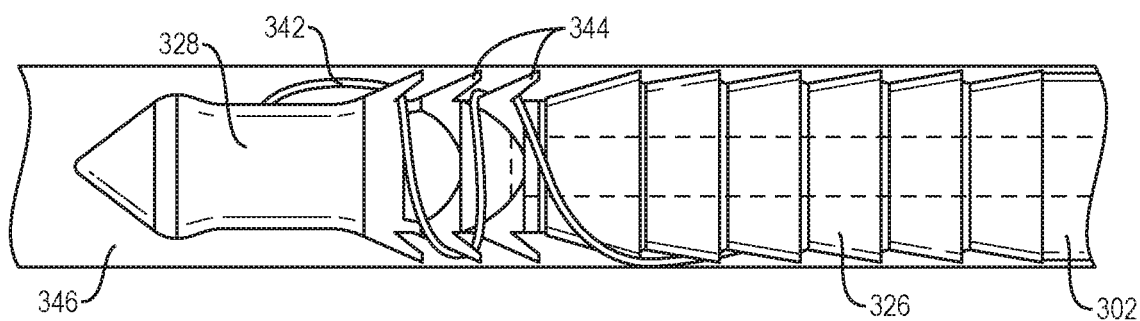

FIG. 12B illustrates the suture securing assembly 300 of FIG. 12A rotated 90 degrees. As shown in FIG. 12B, when the distal anchor body 328 is inserted into a pre-formed bone hole 346, the wings 344 are allowed to outwardly flex such that they compress one or more sutures 342 which have been threaded through the through hole 334 against the surface of the bone hole 346. After insertion of the proximal anchor body 326 into the bone hole 346, the inner shaft 320 of the inserter 302 can then be removed from the proximal anchor body 326 and the distal anchor body 328 by rotation of the inner shaft 320, thus causing rotation of the distal anchor body 328 relative to the proximal anchor body 326. When the distal anchor body 328 is rotated, the suture 342 becomes coiled around the distal anchor body 328, thus taking up slack in the suture 342 and creating additional suture retention by increasing the tortuosity of the suture path. Advantageously, during rotation, additional fixation of the distal anchor body 328 is also created within the bone hole 346 as the wings 344 engage with new, uncompromised bone. In an alternative example, shown in FIG. 12C, the wings 344 on the distal anchor body 328 are oriented such that they do not cross the path of the suture 342, and thus the suture 342 is compressed instead between the bone hole 346 and the proximal anchor body 326.

Figure 12D:
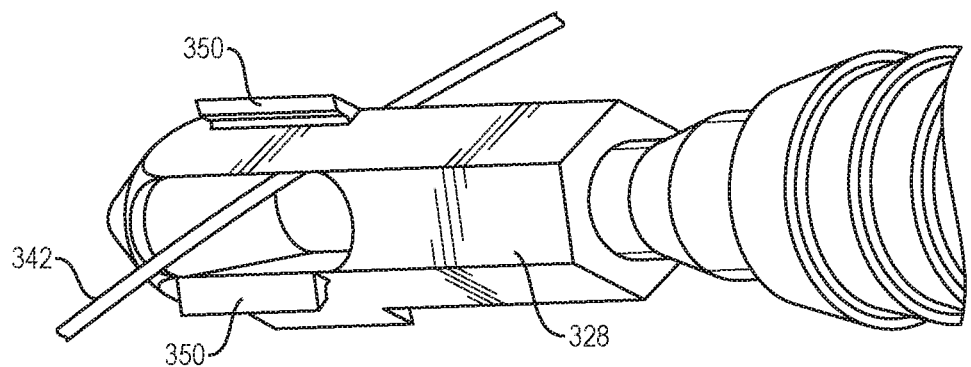
Figure 12E:
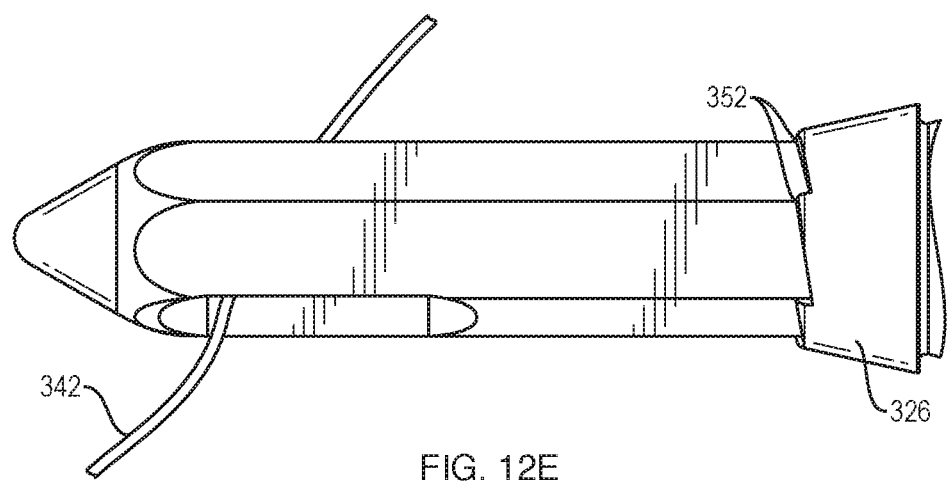

Alternative examples of the rotatable distal anchor body 328 are shown in FIGS. 12D and 12E. In FIGS. 12D and 12E, the distal anchor body 328 is substantially similar to that shown in FIGS. 12A-C except as described below. In FIG. 12D, the distal anchor body 328 has a hexagonal cross-section, although other cross-sectional shapes are contemplated by this disclosure. For example, the distal anchor body 328 may have a circular or elliptical cross-section, or a polygonal shape with more or fewer than six sides. As shown in FIG. 12D, the area around the through hole 334 of the distal anchor body 328 comprises anti-rotation barbs 350. The barbs 350 are made of a material that is capable of flexing in one direction while the distal anchor body 328 is rotated, but is stiffer in the anti-rotation direction. When the suture 342 is put in tension, the barbs 350 have the capability of engaging bone to prevent rotation. In the example of FIG. 12E, both of the distal anchor body 328 and the proximal anchor body 326 have a series of teeth 352 that interact such that, when the proximal anchor body 326 and the distal anchor body 328 are in contact, the distal anchor body 328 may be rotated relative to the proximal anchor body 326, but only in one direction.

Figure 12F:
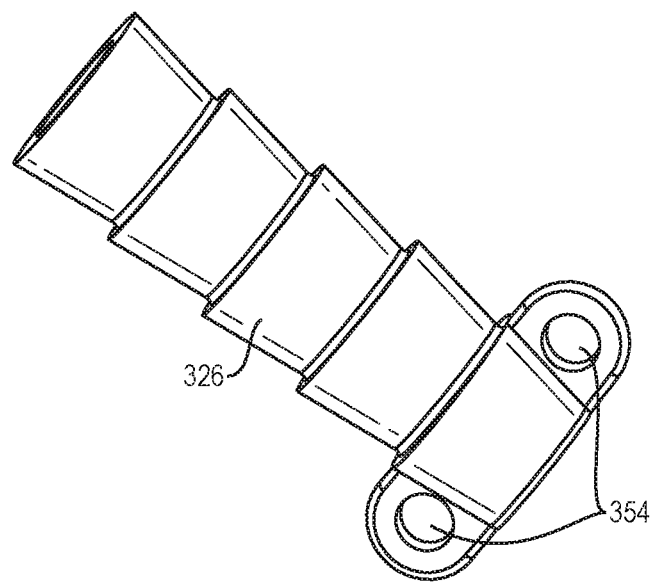

Additional features could also be added to the proximal anchor body 326 to facilitate spooling of the suture 342 around the distal anchor body 328 when the distal anchor body 328 is rotated. The features could be eyelets 354, as shown in FIG. 12F, or posts, in some examples. If the eyelets 354 or other features were combined with an anti-rotation design, the eyelets 354 may advantageously provide a means for the proximal anchor body 326 to counteract the torque imparted on it during the rotation of the distal anchor body 328. Alternatively, in examples (not shown), the proximal anchor body 326 could have features that spool the suture 342 around the proximal anchor body 326 if the distal anchor body 328 is held stationary while the proximal anchor body 326 is rotated.

As discussed above, the suture anchor assemblies 100, 200, 300 use threaded joints to rigidly couple the distal anchor body to the inserter. However, when a surgeon attempts to align the inserter to the trajectory of a pre-drilled bone hole, an anchor body that is rigidly coupled to the inserter may sometimes experience excessive strain and be damaged if the trajectory is slightly off-axis. It would therefore be advantageous in certain applications if the distal anchor body and the inserter were adapted for threadless engagement with each other, for example, with a friction fit.

Figure 13A:
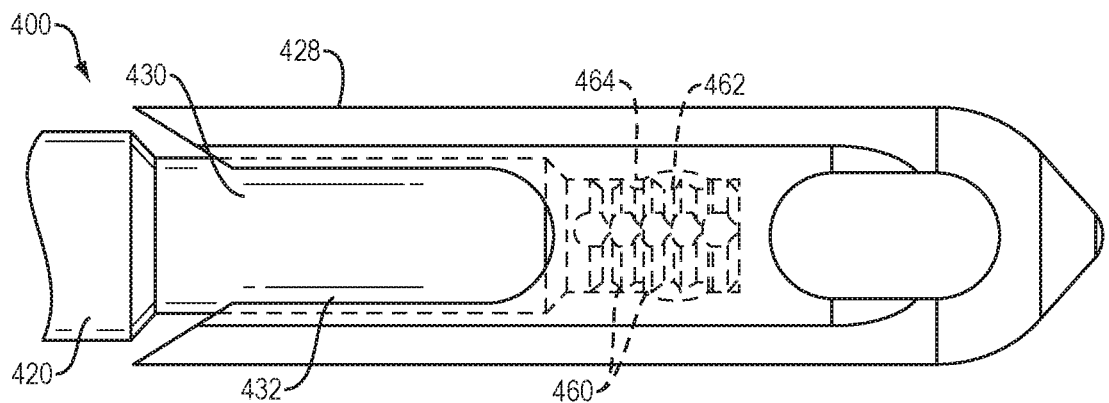
FIGS. 13A-14 illustrate alternative interfaces between the inner shaft and the distal anchor body of the suture securing assemblies of this disclosure.
Figure 13B:
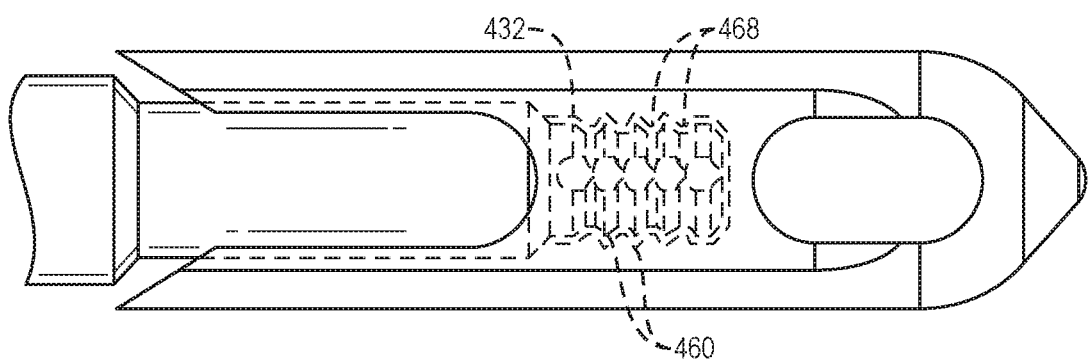

FIG. 13A illustrates another example of a suture securing assembly 400 of this disclosure. The suture securing assembly 400 is substantially similar to the suture anchor assemblies 100, 200, 300 except as described below. In FIG. 13A, the distal anchor body 428 is shown as mounted to the inserter inner shaft 420 prior to use. The distal portion 430 of the inner shaft 420 extends into the cavity 432 of the distal anchor body 428. Rather than threads, however, a plurality of barbs 460 is formed along an outer surface of the distal portion 430. The inner surface of the cavity 432 in turn has a corresponding hole 462 for pressing over the barbs 460. In examples, the barbs 460 are flexible such that the distal portion 430 can be inserted into the cavity 432 to form a friction fit between the barbs 460 and the cavity 432. However, a pullout force of the inner shaft 420 is resisted as the barbs 460 engage the annular lip 464 formed between the hole 462 and the cavity 432. Under normal use conditions, this pullout force can only be overcome once the distal anchor body 428 has been placed into bone and a proximal force is applied to the inner shaft 420 sufficient to overcome the resistance. In other examples, the inner shaft 420 and/or the barbs 460 may be made of a rigid material, such as metal, while the distal anchor body 428 is made of a polymer, such as PEEK. When the inner shaft 420 is inserted into the cavity 432, the distal anchor body 428 deforms about the metal barbs 460, forming a friction fit between the inner shaft 420 and the distal anchor body 428. In still other examples, illustrated in FIG. 13B, the inner surface of the cavity 432 may comprise a number of undercuts 468 configured to receive the barbs 460.

Figure 13C:
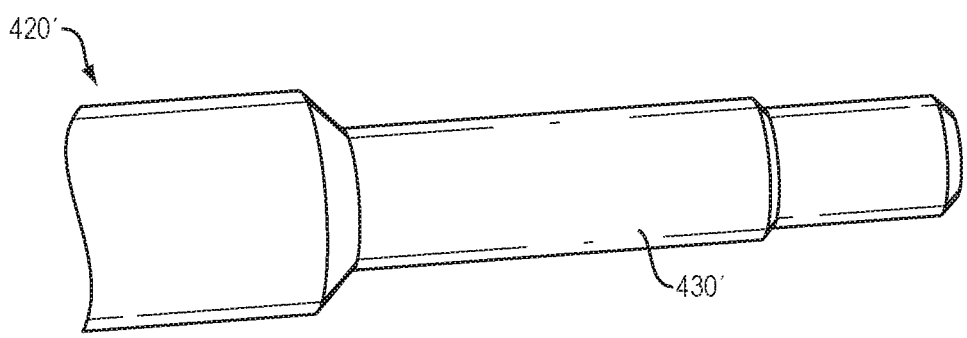

An alternative example of an inserter inner shaft 420' is shown in FIG. 13C. The inner shaft 420' is similar to the inner shaft 420 except that mechanical engagement between the distal anchor body (not shown) and the inner shaft 420' may be a conventional press fit. For example, the distal portion 430' of the inner shaft 420' may have a stepped-down geometry with sections of decreasing diameter to mate with corresponding sections increasing diameter of the cavity of the anchor body. Additionally, the distal portion 430' of the inner shaft 420' may have an intentionally rough surface (e.g. sandblasted, hammered, rough machined, etc.) in order to increase the strength of the mechanical engagement between the distal anchor body and the inner shaft 420'. In alternative examples, not shown, the distal portion 430' of the inner shaft 420' can have specific features to prevent rotation of the distal anchor body relative to the inner shaft 420', such as splines or ribs.

Figure 14:
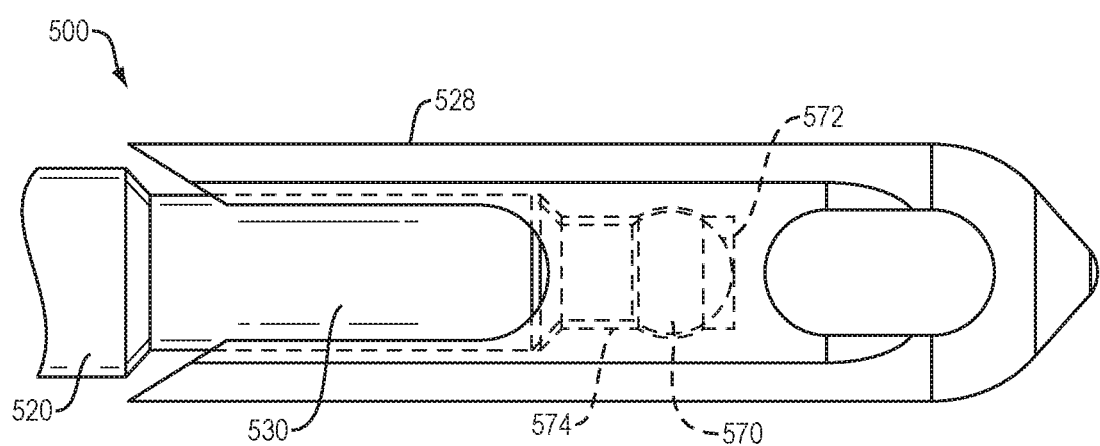

Turning now to FIG. 14, another example of a suture securing assembly 500 of this disclosure is shown. Suture securing assembly 500 is substantial similar to suture securing assemblies 100, 200, 300, 400 except as described below. In suture securing assembly 500, the mechanical engagement between the distal anchor body 528 and the inner shaft 520 is a threadless joint between the distal portion 530 of the inner shaft 520 and the cavity 532 that permits articulation of the distal anchor body 528. For example, the distal portion 530 includes a hemispherical distal end 570. The cavity 532 in turn has a corresponding hemispherical socket 572 for moveably coupling to the distal end 570 of the distal portion 530. Thus, a pullout force of the inner shaft 520 is resisted by the distal end 570 of the distal portion 530 engaging the annular lip 574 formed between the socket 572 and the cavity 532. Under normal use conditions, this pullout force can only be overcome once the distal anchor body 528 has been placed into bone and a proximal force is applied to the inner shaft 520 sufficient to overcome the resistance. This "ball-and-socket" engagement may advantageously permit additional degrees of freedom between the distal anchor body 528 and the inner shaft 520 about any axis, compared to the degrees of freedom provided by a threaded or a press fit joint.

In examples, not shown, the articulating joint may not be limited to a ball-and-socket joint, but could be a pin joint, a sliding joint, or any number of universal joints. The articulating joint could also be made with a living hinge on the cavity 532 or the distal portion 530 of the inner shaft 520. It is further contemplated that the articulating joint could exist between the proximal anchor body (not shown) and the distal anchor body 528, rather than the distal anchor body 528 and the inner shaft 520. The articulating joint could further be accomplished by reducing the cross-section of the distal portion 530 of the inner shaft 520 substantially enough to allow flex, while the cavity 532 of the distal anchor body 528 has a mating geometry that allows this flex.

Figure 15A:
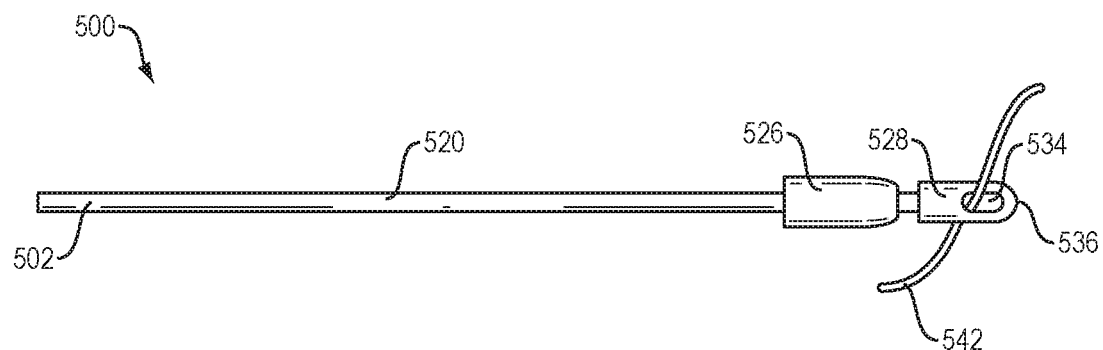
FIGS. 15A and 15B illustrate the use of the suture securing assembly of FIG. 14 during a soft tissue repair.

Turning now to FIG. 15A, an example of the suture securing assembly 500 is illustrated during use in a soft tissue repair. In FIG. 15A, the proximal anchor body 526 is disposed on the inner shaft 520 of the inserter 502 and the distal anchor body 528 is disposed at the distal end of the inner shaft 520. A suture 542 is positioned within the through hole 534, such that one or more free limbs of the suture 542 extend outward from the through hole 534. In examples, the tip 536 of the distal anchor body 528 is also useable by a surgeon as a probe to tactilely identify the location of a bone hole. However, it is notable that this tactile identification can sometimes cause misalignment of the distal anchor body 328 to the trajectory of the bone hole.

Figure 15B:
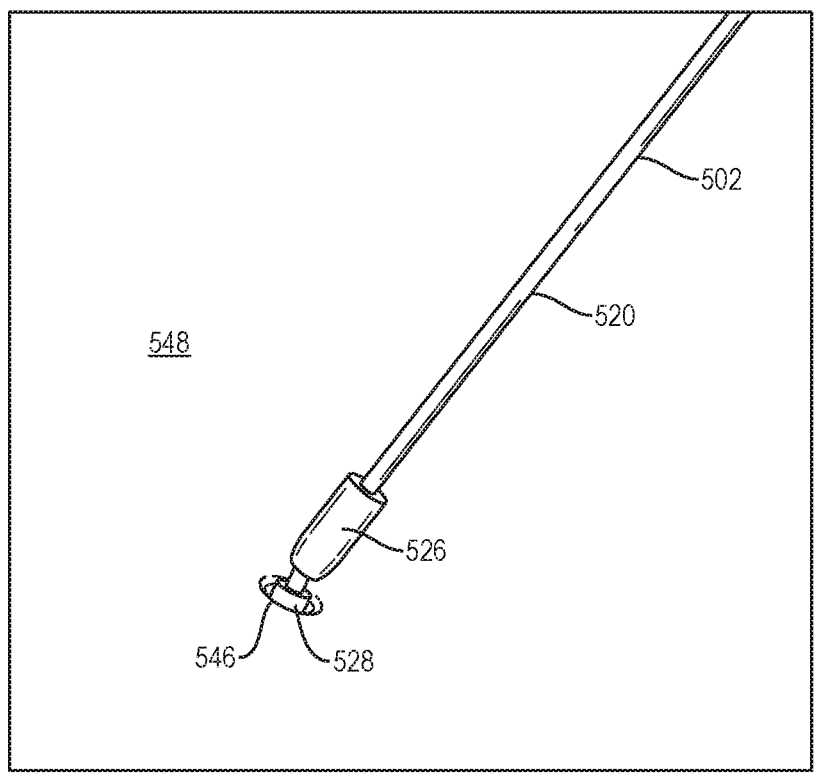

As shown in FIG. 15B, to begin the repair, at least a portion of the distal anchor body 528 is inserted into a pre-formed bone hole 546 formed within bone 548. During this insertion process, at least one of the free limbs of the suture (not shown) is positioned so as to be impinged between the distal anchor body 528 and the walls of the bone hole 546. Beneficially, the distal anchor body 528 is supported by the inner shaft 520, providing a mechanical durability that allows the surgeon to move soft tissue and/or bone with the tip 536 of the distal anchor body 528. Additionally, the articulating joint between the distal anchor body 528 and the inner shaft 520 advantageously accommodates any misaligned trajectory, thus decreasing the likelihood of causing damage to the distal anchor body 528 during insertion into the bone hole 546. Once the distal anchor body 528 and proximal anchor body 526 have been inserted into the bone hole 546, the inserter 502 can then be removed applying a counterforce sufficient to overcome the resistance created by the articulating joint.

In the examples described above, the suture securing assemblies 100, 200, 300, 400, 500 can be used to pretension a suture during use in a surgical repair. However, in some repairs, it may be preferable to sacrifice the pre-tensionability of the assembly for the sake of a more robust (i.e. larger) distal anchor body, and for simplicity (i.e., fewer steps) in the repair process. Additionally, it may be desirable to deploy the expansion wings 140 on the distal anchor body 128 of FIG. 2 in a single step, rather than in a two-stage retraction process, as described above.

Figures 16A, 16B:
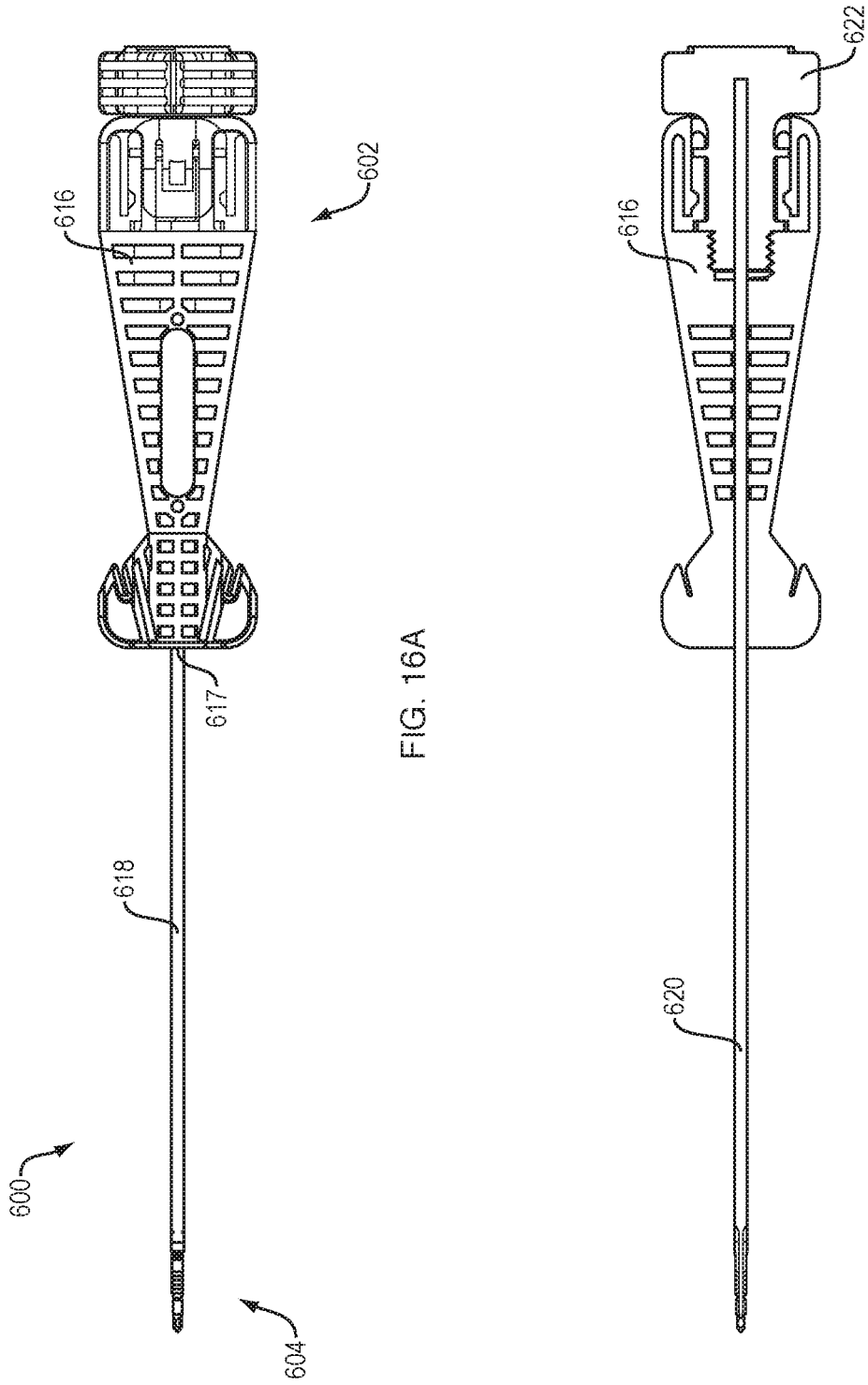
FIGS. 16A-E illustrate an alternative suture securing assembly of this disclosure.

FIGS. 16A-D illustrate another example of a suture securing assembly 600 according to the present disclosure. The suture securing assembly 600 is substantially similar to the suture securing assemblies 100, 200, 300, 400, 500 except as described below. As shown in FIG. 16A, the suture securing assembly 600 generally comprises an inserter 602 and a two-bodied anchor 604. The inserter 602 comprises a handle 616 and an outer shaft 618 fixedly attached to the distal end 617 of the handle 616. FIG. 16B is a cutaway view of the suture securing assembly 600 of FIG. 16A. As shown in FIG. 16B, an inner shaft 620 extends from the distal end of the outer shaft 618 (not shown). A knob 622 is threadingly coupled to the handle 616 and is rotatable independent of the handle 616. The inner shaft 620 is fixedly attached to the knob 622 such that it is both axially and rotationally moveable independent of the outer shaft 618 by rotation of the knob 622.

Figure 16C:
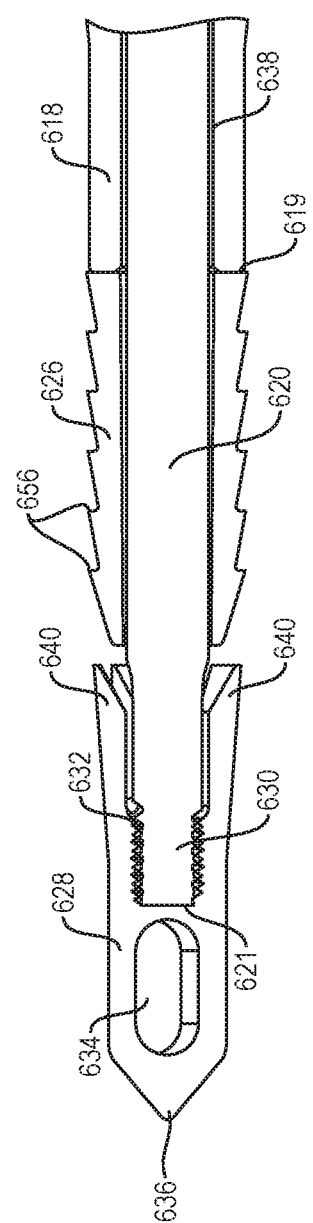

Turning now to FIG. 16C, a detailed, cutaway view of the outer shaft 618, the inner shaft 620, the proximal anchor body 626 and the distal anchor body 628 is shown. As illustrated in FIG. 16C, a cannulated proximal anchor body 626 is disposed on the inner shaft 620 near the distal end 619 of the outer shaft 618, and a distal anchor body 628 is disposed on the inner shaft 620 near a distal end 621 of the inner shaft 620. Either or both of the proximal anchor body 626 and the distal anchor body 628 can be sized appropriately for instability or rotator cuff repair. Unlike the distal anchor body 128 of FIG. 1, however, a diameter of the distal anchor body 628 is selected to be about the same as a diameter of the proximal anchor body 626. Either or both of the proximal anchor body 626 and the distal anchor body 628 can be made from any combination of metal, PEEK, bioabsorbable, or biocomposite material.

Still referring to FIG. 16C, the inner shaft 120 is slidably disposed in, and extends from, a channel 638 in the outer shaft 618. The proximal anchor body 626 may comprise barbs 656 or other surface features which help it anchor into bone. In examples, the proximal anchor body 626 may be locked into position relative to the outer shaft 618 by a press fit (i.e., friction) between the proximal anchor body 626 and the inner shaft 620, or by a threaded interface with the inner shaft 620, such that the proximal anchor body 626 resists proximal movement under normal use conditions. In the example of FIG. 16C, the distal end 621 of the inner shaft 620 comprises a threaded portion 630 for mating with a threaded interior cavity 632 of the distal anchor body 628. In other examples, the interface between the inner shaft 620 and the cavity 632 may comprise a non-threaded interface, such as those described with regard to FIGS. 13A-14. The cavity 632 extends from a proximal end of the distal anchor body 628 to a region proximal to a transverse through hole 634 configured for passage of a suture. In examples, the distal anchor body 628 also has a pointed tip 636 for being driven into bone, and expansion wings 640, described in further detail below.

Figure 16D:
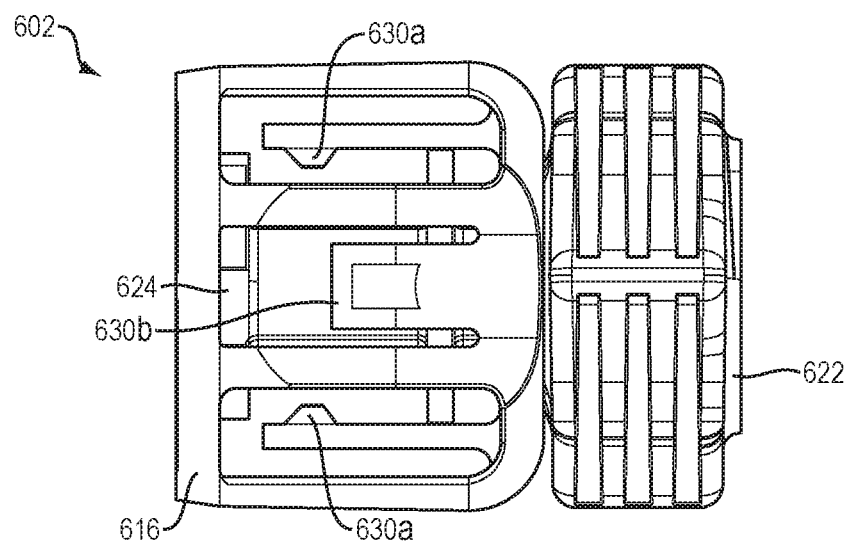
Figure 16E:
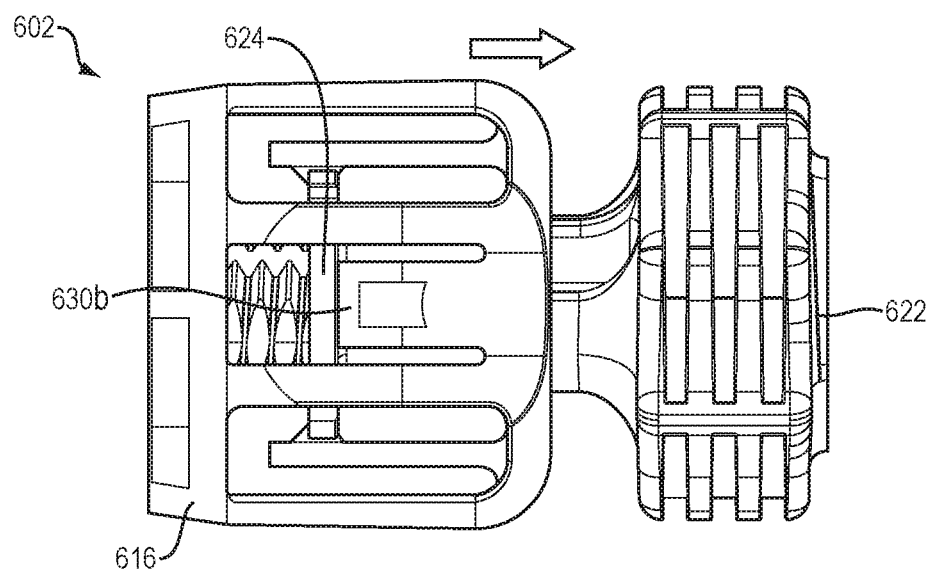

FIGS. 16D and 16E are a detailed, cutaway views of the proximal end of the inserter 602 of FIG. 16A. As stated above, rotation of the knob 622 causes rotation and/or retraction of the inner shaft relative to the handle 616. As retraction occurs, a distal disc 624 on the knob 622 engages with a first set of snap features 630a on the handle 616 (FIG. 16D). The snap features 630a interact with ratchet features on the distal disc 624, described in more detail below. The interaction of these features causes an audible and tactile feedback that signals to the surgeon they are using the device correctly. Upon retraction, the distal disc 624 on the knob 622 eventually interacts with a second set of snap features 630b on the handle 616 (FIG. 16E). The snap features 630b provide a hard stop against the distal disc 624, preventing the knob 622 from further rotation or axial motion, as further described below.

FIGS. 17A-D illustrate the use of the suture securing assembly 600 of FIGS. 16A-E during a soft tissue repair. In FIGS. 17A-D, the suture securing assembly 600 is used for a shoulder instability (labral) repair. However, it is contemplated by this disclosure that the suture securing assembly 600 could be adapted or scaled for other types of surgical repair.

Figure 17A:
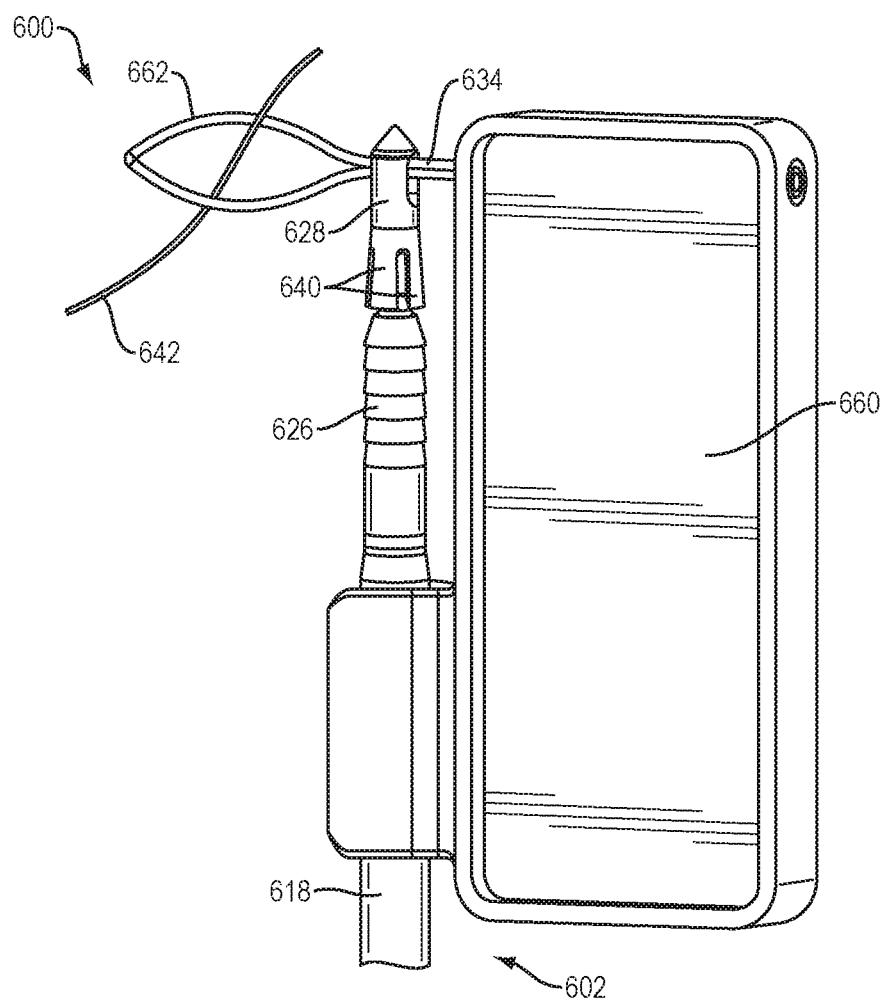
FIGS. 17A-D illustrate the use of the suture securing assembly of FIG. 16A during a soft tissue repair.

FIG. 17A illustrates the suture securing assembly 600 attached to a suture threader 660. In examples, the suture threader 660 is initially clipped onto the outer shaft 618 of the assembly 600 with a wire loop 662 of the suture threader 660 extending through the through hole 634 of the distal anchor body 628. The suture threader 660 may be used to pull a length of suture 642 through the through hole 634. To begin the repair, the suture 642 is first passed through soft tissue (not shown). The suture 642 is then passed through the through hole 634 of the distal anchor body 628 with or without the aid of the suture threader 660. A hole is then prepared in bone (not shown) and the distal anchor body 628 is approximated to the hole. The suture 642 is then appropriately tensioned. Both of the proximal anchor body 628 and the distal anchor body 628 are then inserted into the bone hole, for example, by pounding the inserter 602 with a mallet, thus compressing the suture 642 between the distal anchor body 626 and the bone hole to lock the suture 642 in the bone hole. The knob 622 of the handle 616 (FIG. 16D) is then rotated, retracting the distal anchor body 628 toward the proximal anchor body 626, deploying the expansion wings 640.

Figure 17B:
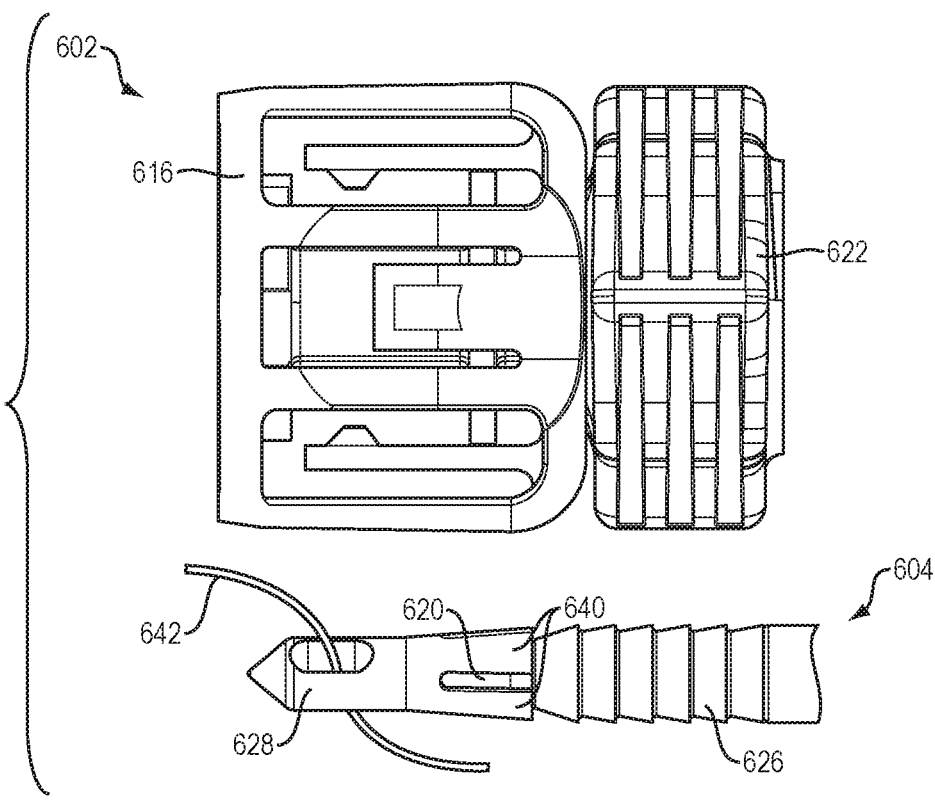
Figure 17C:
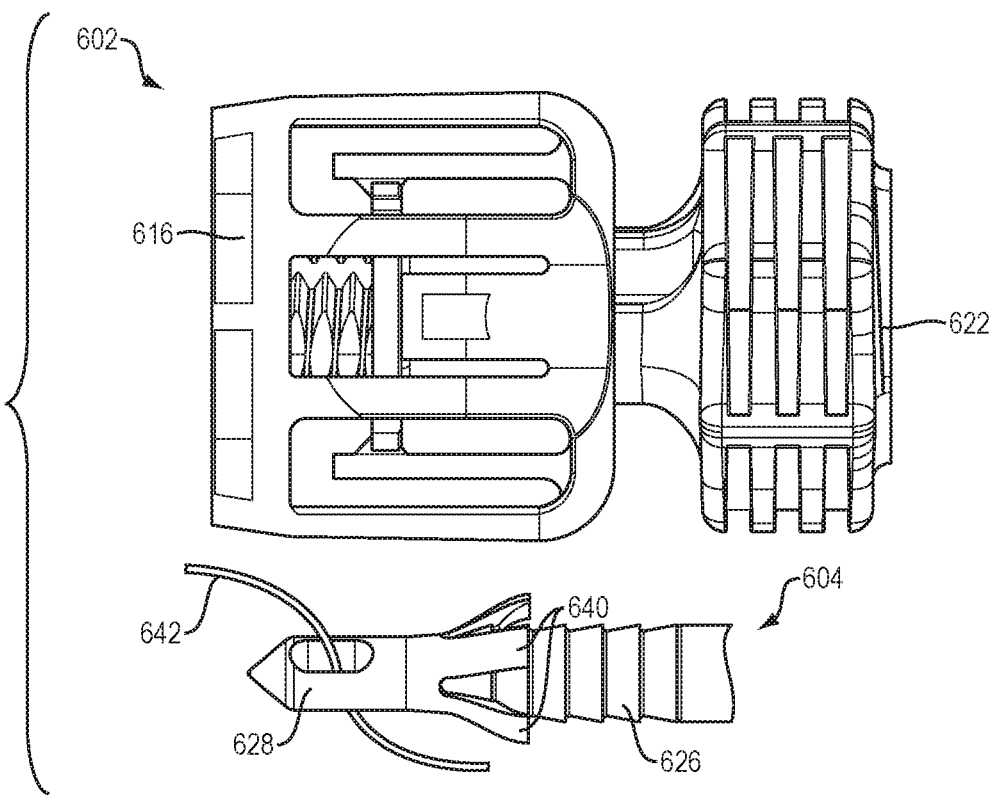

FIGS. 17B and 17C illustrate the deployment of the expansion wings 640 while the knob 622 is being rotated. As stated above, rotation of the knob 622 causes rotation and/or retraction of the inner shaft 620 (FIG. 17B). Because the inner shaft 620 is connected via a threaded joint to the distal anchor body 628, the distal anchor body 628 is also forced to rotate and retract. When the distal anchor body 628 retracts, the expansion wings 640 encounter the tapered distal end of the proximal anchor body 626, which forces the wings 640 to expand radially (FIG. 17C). This radial expansion of the wings 640 causes an increase in compression against the bone (not shown) and further compresses the length of suture 642 against the bone hole, providing additional suture lock.

Figure 17D:
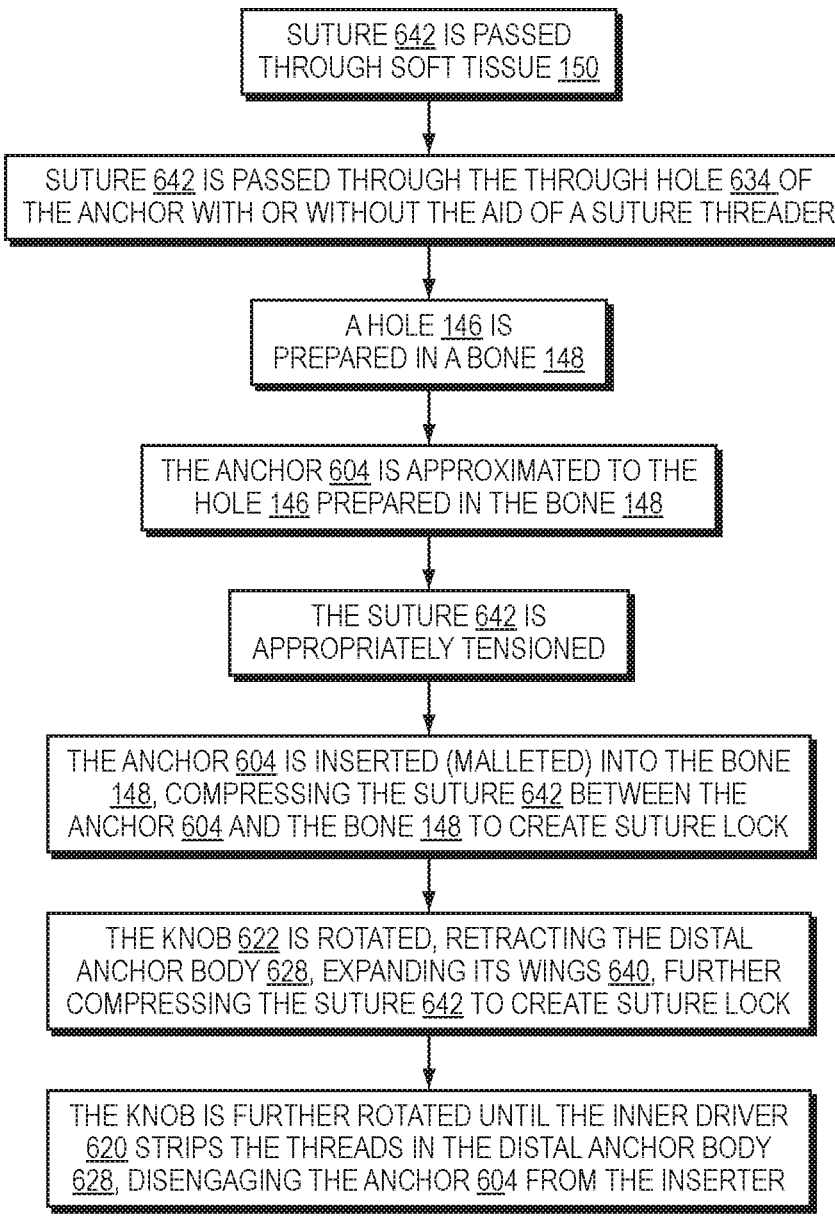

Notably, when the interface between the inner shaft 620 and the distal anchor body 628 is a threaded interface, the knob 622/handle 616 and inner shaft 620/distal anchor body 628 are both threaded in opposite directions (i.e., right-handed threads on the distal anchor body 628 and left-handed threads on the knob 622). If the threads were both in the same direction (both right-handed or both left-handed threads), rotation of the knob 622 would simply unscrew the inner shaft 620 from the distal anchor body 628. Instead, rotation of the knob 622 causes the inner shaft 620 to further screw into the cavity 632 of the distal anchor body 628. Because the inner shaft 620 is fully threaded into the blind cavity 632, it cannot screw in any further. This, in effect, causes the distal anchor body 628 to become fixedly attached to the inner shaft 620. Eventually, the distal anchor body 628 engages fully against the proximal anchor body 626 and is prevented from further retraction. Further rotation of the knob 622 and further retraction of the inner shaft 620 causes eventual failure of the threaded joint on the distal anchor body 628 and disengagement of the inner shaft 620 from the distal anchor body 628. The inner shaft 620 continues to retract until the inner shaft 620 is almost entirely clear of the proximal anchor body 626, stopping when the knob 622 encounters the snap features 630a, 630b (FIG. 16B). The inserter 602, now completely disconnected from both the proximal anchor body 626 and the distal anchor body 628, can be removed from the repair site. FIG. 17D is a flowchart of the steps used in the soft tissue repair as described above.

Figure 18A:
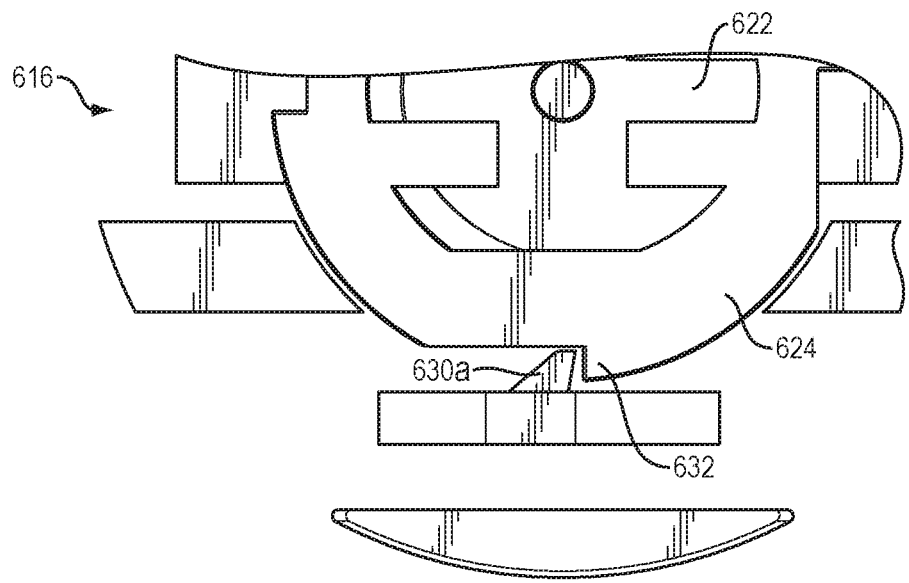
FIGS. 18A-D are detailed, cutaway views of the snap features of the handle of the suture securing assembly of FIG. 16A.
Figure 18B:
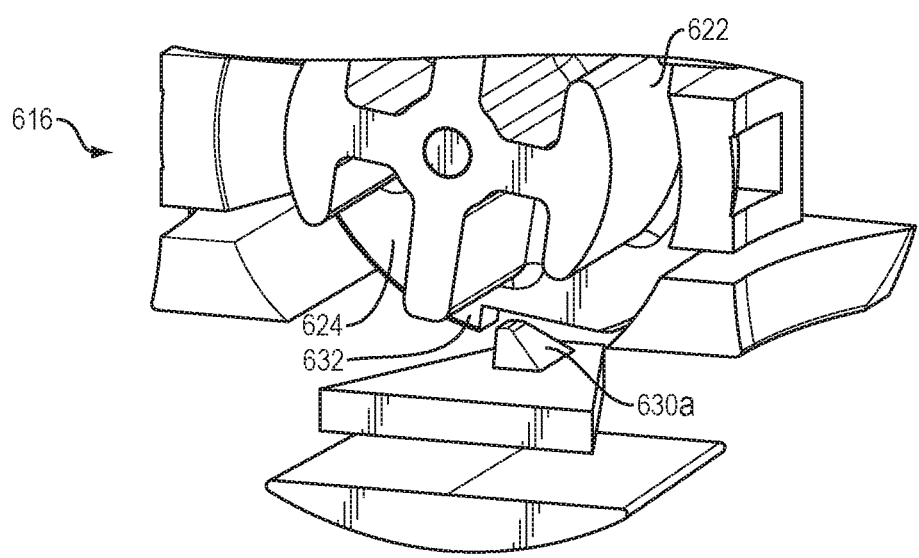

FIGS. 18A and 18B show detailed, cutaway views of the snap features 630a. As discussed above, the distal disc 624 of the knob 622 has ratchet features 632 located in several positions about the distal disc 624 such that a ratchet feature 632 will interface with a snap feature 630a every 90 degrees. The ratchet features 632 act as ramps, lifting the snap features 630a as the knob 622 is turned. At the end of the ratchet features 632, the snap features 630a encounter a sudden drop. Because the snap features 630a have been loaded (i.e., given potential energy), the snap features 630a quickly accelerate off the ratchet features 632 and impact the surface below, causing vibration of the handle 616. These effects produce both tactile and audible signals to the user.

Figure 18C:
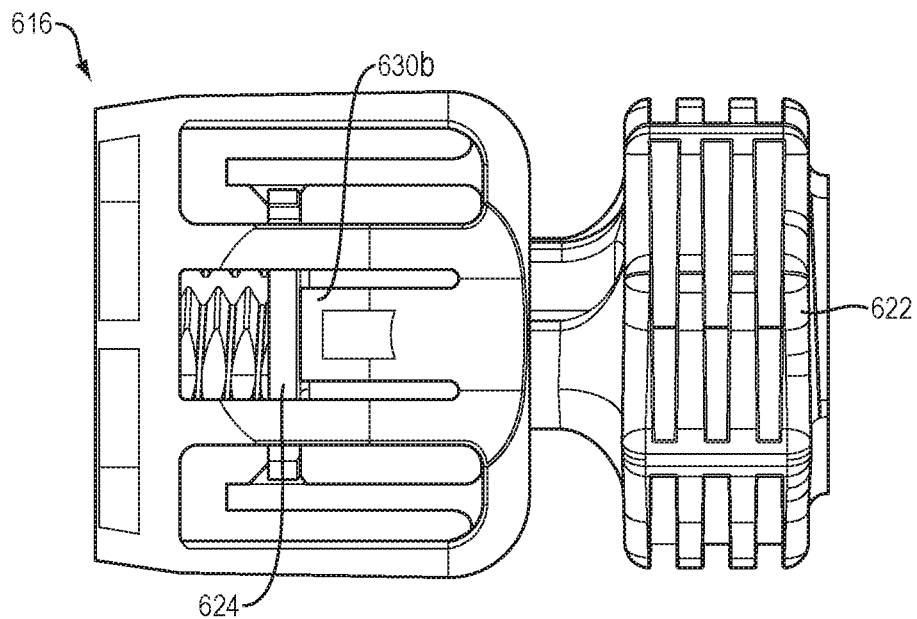
Figure 18D:
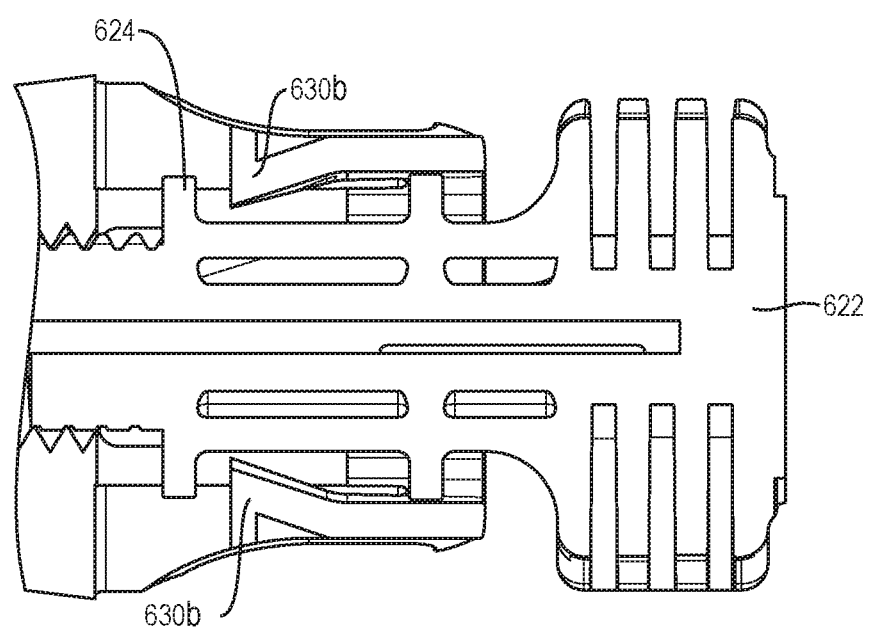

FIG. 18C further details the interaction between the distal disc 624 and the snap features 630b of the handle 616, as discussed above. In FIG. 18C, two snap features 630b are oriented 180 degrees from each other. The snap features 630b act as one-way ramps, such that the knob 622 can be pushed past the snap features 630b during assembly, but cannot proceed in the other direction during rotation of the knob 622. The distal disc 624 eventually engages the snap features 630b, preventing the knob 622 from further rotation and/or retraction. FIG. 18D shows the ramp profile of the snap features 630b in further detail.

In certain examples, the suture securing assemblies of this disclosure may be provided to a user as a kit, including the anchor and the inserter pre-assembled. Such a configuration is beneficial for completely disposable systems, where the inserter is discarded after being used to insert the attached anchor. In alternative examples, the anchor and the inserter may be provided separately and subsequently assembled. Such a configuration is beneficial for partially reusable systems, where the inserter is saved and reconditioned for further use after being employed to insert an anchor that has been attached thereto.

The disclosure has been described with reference to the preferred embodiments. Obviously, modifications and alterations will occur to others upon reading and understanding the preceding detailed description. It is intended that the disclosure be construed as including all such modifications and alterations insofar as they come within the scope of the appended claims or the equivalents thereof.

What is claimed is:

1. A suture securing assembly, comprising:
    an inserter comprising:
        a handle;
        an outer shaft fixedly coupled to the handle, the outer shaft having a proximal end, a distal end, and a longitudinal axis extending therebetween, the outer shaft defining an internal cannulation extending between the proximal and distal ends; and
        an inner shaft disposed within the cannulation such that a portion of the inner shaft extends from the distal end of the outer shaft, the inner shaft axially moveable relative to the outer shaft; and
    an anchor comprising:
        a cannulated proximal body disposed on the inner shaft of the inserter; and
        a distal body disposed on a distal end of the inner shaft, the distal body having a through hole defined through the distal body transverse to the longitudinal axis for passage of a suture;
    wherein the distal body is moveable by the inner shaft in a proximal but not a distal direction relative to the proximal body.

2. The assembly of claim 1, wherein the handle comprises a rotatable knob coupled to the handle, the knob attached to the inner shaft for retracting the inner shaft relative to the outer shaft.

3. The assembly of claim 1, wherein at least one of the proximal body and the distal body is made from any combination of metal, polymer, bioabsorbable, or biocomposite material.

4. The assembly of claim 1, wherein a cavity of the distal body defines a first locking feature and the inner shaft defines a second locking feature for mechanical engagement with the first locking feature.

5. The assembly of claim 4, wherein the first locking feature is a first plurality of threads formed on an inner surface of the cavity, and the second locking feature is a second plurality of threads formed on an outer surface of the inner shaft, the second plurality of threads configured to mate with the first plurality of threads.

6. The assembly of claim 4, wherein the first locking feature is a hole formed in the cavity and the second locking feature is a plurality of barbs on an outer surface of the inner shaft, the hole configured to press over the barbs.

7. The assembly of claim 4, wherein the engagement between the first locking feature and the second locking feature allows articulation of the distal body relative to the proximal body about any axis.

8. The assembly of claim 1, wherein the distal body comprises expansion wings for engagement with a prepared bone hole.

9. The assembly of claim 1, further comprising a flexible strand in the form of a closed loop extending through the through hole, the flexible strand for coupling to a suture.

10. The assembly of claim 9, wherein the flexible strand comprises at least one of suture, plastic and malleable metal.

11. The assembly of claim 1, wherein a surface of the distal body between the proximal end and the through hole comprises a plurality of passive wings, the passive wings being outwardly flexible upon insertion into bone.

12. The assembly of claim 11, wherein the passive wings are comprised of one of PEEK, other plastics, and metals.

13. The assembly of claim 1, wherein the distal body and/or the proximal body comprises features for allowing rotation of the distal body relative to the proximal body in a first direction, but preventing rotation of the distal body relative to the proximal body in a second direction.

14. A method of securing a suture in a bone hole, the method comprising:
    passing a length of suture through a through hole of a distal body of an anchor, the distal body comprising a proximal end, a distal end and a longitudinal axis extending therebetween, the through hole defined through the distal body transverse to the longitudinal axis;
    placing the distal body at the bottom of a bone hole, a proximal body of the anchor being separated by a distance from the distal body such that the proximal body is located outside of the bone hole;
    tensioning the length of suture;
    inserting a portion of the proximal body into the bone hole such that legs of the length of suture are fixed between the proximal body and the bone hole, the distance between the proximal body and the distal body remaining unchanged;
    retracting the distal body toward the proximal body, creating suture slack in the bone hole; and
    driving the distal body and the proximal body together into the bone hole, thereby removing the suture slack in the bone hole.

15. The method of claim 14, wherein the distal body is spaced apart from the proximal body of the anchor along a length of an inner shaft of an inserter, and wherein retracting the distal body toward the proximal body comprises retracting the inner shaft relative to a handle of the inserter.

16. The method of claim 14, wherein, when driving the distal body and the proximal body together into the bone hole, there is no relative motion between the distal body and the proximal body.

17. A method of securing a suture in a bone hole, the method comprising:
    passing a length of suture through a through hole of a distal body of an anchor, the distal body comprising a proximal end, a distal end and a longitudinal axis extending therebetween, the through hole defined through the distal body transverse to the longitudinal axis, the anchor comprising a cannulated proximal body disposed on an inner shaft of an inserter near a distal end of an outer shaft of the inserter, the distal body disposed on the inner shaft near a distal end of the inner shaft, the distal body having radially expanding wings at a proximal end;
    approximating the distal body to a bone hole;
    tensioning the length of suture;

inserting the proximal body and the distal body into the bone hole, the distance between the proximal body and the distal body remaining unchanged;

retracting the distal body toward the proximal body by retracting the inner shaft relative to a handle of the inserter using a rotatable knob coupled to the inner shaft such that the wings engage the proximal body, causing the wings to radially expand; and further retracting the inner shaft using the rotatable knob such that the proximal body and the distal body are disengaged from the inner shaft;

wherein the length of suture is compressed between the distal body and the bone hole.

18. The method of claim 17, wherein passing the length of suture through the through hole of the distal body comprises passing the length of suture with a suture threader.

19. The method of claim 17, wherein the inner shaft is coupled to a knob of a handle, and wherein retraction of the inner shaft comprises rotating the knob of the handle.

20. The method of claim 19, wherein the handle comprises a first set of features for engagement with a second set of features on the knob, the engagement providing audible and tactile feedback to a user.

21. The method of claim 19, wherein the handle comprises a stop feature for limiting retraction of the inner shaft relative to the handle.

22. The method of claim 17, further comprising passing the length of suture through tissue.

\* \* \* \* \*